US008293938B2

(12) United States Patent
Hill et al.

(10) Patent No.: US 8,293,938 B2
(45) Date of Patent: Oct. 23, 2012

(54) ALKYLPHOSPHONOUS ACIDS, SALTS AND ESTERS, METHODS FOR THE PRODUCTION THEREOF, AND USE OF THE SAME

(75) Inventors: Michael Hill, Cologne (DE); Harald Bauer, Kerpen (DE); Werner Krause, Huerth (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 12/668,814

(22) PCT Filed: Jul. 2, 2008

(86) PCT No.: PCT/EP2008/005382
§ 371 (c)(1),
(2), (4) Date: Jan. 12, 2010

(87) PCT Pub. No.: WO2009/010188
PCT Pub. Date: Jan. 22, 2009

(65) Prior Publication Data
US 2010/0190901 A1 Jul. 29, 2010

(30) Foreign Application Priority Data

Jul. 13, 2007 (DE) .................. 10 2007 032 669

(51) Int. Cl.
C07F 9/28 (2006.01)
(52) U.S. Cl. .............. 562/8; 524/126; 524/133; 558/89; 558/104; 558/105; 558/108; 558/110; 558/137; 558/177; 558/179; 568/8
(58) Field of Classification Search .................. 524/126, 524/133; 558/89, 104, 105, 108, 110, 137, 558/177, 179; 562/8; 568/8
See application file for complete search history.

(56) References Cited

U.S. PATENT DOCUMENTS

| 2,957,931 | A | | 10/1960 | Hamilton et al. | |
|---|---|---|---|---|---|
| 3,914,345 | A | | 10/1975 | Kleiner et al. | |
| 4,088,678 | A | | 5/1978 | Matt et al. | |
| 4,740,332 | A | * | 4/1988 | Thottathil | 562/8 |
| 5,051,413 | A | | 9/1991 | Angst et al. | |
| 5,175,344 | A | | 12/1992 | Angst et al. | |
| 5,457,095 | A | | 10/1995 | Dingwall et al. | |
| 5,663,139 | A | | 9/1997 | Stowasser et al. | |
| 5,734,072 | A | | 3/1998 | Kleiner et al. | |
| 5,891,226 | A | * | 4/1999 | Kleiner et al. | 106/18.18 |
| 5,973,194 | A | * | 10/1999 | Weferling et al. | 562/8 |
| 6,090,967 | A | * | 7/2000 | Horold et al. | 558/105 |
| 6,090,968 | A | * | 7/2000 | Horold et al. | 558/137 |
| 6,278,012 | B1 | | 8/2001 | Horold et al. | |
| 6,329,544 | B1 | * | 12/2001 | Weferling et al. | 562/8 |
| 6,770,779 | B1 | * | 8/2004 | Weferling et al. | 562/8 |
| 6,806,383 | B1 | * | 10/2004 | Weferling et al. | 562/8 |
| 6,815,558 | B1 | * | 11/2004 | Weferling | 562/8 |
| 7,285,587 | B2 | * | 10/2007 | Strand et al. | 524/126 |

FOREIGN PATENT DOCUMENTS

| CA | 1178388 | 11/1984 |
|---|---|---|
| DE | 2100779 | 7/1972 |
| DE | 4220566 | 1/1994 |
| DE | 19604195 | 4/1997 |
| EP | 0233154 | 8/1987 |
| EP | 1055677 | 11/2000 |
| EP | 1055679 | 11/2000 |
| WO | WO 01/19837 | 3/2001 |

OTHER PUBLICATIONS

PCT International Search Report for PCT/EP2008/005382, mailed Sep. 27, 2009.
Sasse K: "Houben-Weyl Methoden der Organischem Chemie" Methoden der Organischen Chemie Orgenische Phosphor-Verbindungen XII/I Georg Thieme Verlag, Stuttgart, DE Bd. 12/1, pp. 257-259, 261, 294-301; XP 002500739 (1963).
Nifant'ev et al. "Reactions of Acetylenes with Hypophosphorous and Phosphorous Acids," Journal of General Chemistry USSR Consultants Bureau, NY, NY, US, Bd. 56, Nr. 4, pp. 680-688, XP002165520 (Sep. 20, 1986).
Altamirano et al. "Palladium-Catalyzed Dehydrative Allylation of Hypophosphorus Acid with Allylic Alcohols," Organic Letters, Bd. 8, Nr. 18, pp. 4169-4171, XP 002500860 (2006).
Deprele et al., "Dnivironmentally Benign Synthesis of H-Phosphinic Acids Using a Water-Tolerant, Recyclable Polymer-supported Catalyst" organic Letters Bd. 6, Nr. 21, pp. 3805-3808 XP 002500861 (2004).
Deprele et al., "Palladium-Catalyzed Hydrophosphinylation of Alkenes Alkynes," J. Am. Chem. Soc., Bd. 124 Nr. 32 pp. 0386, 9387 XP 002500862 (2002).
Altamiranoa et al. "A Novel approach to Phosphonic Acids from Hypophosphorous Acid" Tetrahedron Letters, Bd. 48, Nr. 33 pp. 5755-5759 XP 002500863, (Jun. 23, 2007).
Ribiere et al. "MoCl$_2$—Catalyzed Hydrophosphinylation" J. Org. Chem. Bd. 70, Nr. 10, pp. 4064-4072 XP 002530191 (2005).
Thomas et al. "Alkylation of H-Phosphinate Esters under Basic Conditions" J. Org. Chem, Bd. 72 pp. 2851-2856 XP 002530192 (2007).
English Translation of PCT International Preliminary Report on Patentability for PCT/EP 2008/005382, Feb. 9, 2010.

* cited by examiner

*Primary Examiner* — Peter Szekely
(74) *Attorney, Agent, or Firm* — Anthony A. Bisulca

(57) ABSTRACT

The invention relates to alkylphosphonous acids, salts and esters of formula (I) A-P(=O)(OX)—H (I) wherein A is $C_2$-$C_{20}$ alkyl, $C_2$-$C_{20}$ alkylene, and $C_8$-$C_{20}$ alkaryl are optionally substituted, and X is H, alkyl, aryl, alkylaryl, alkenyl, substituted alkyl, aryl, alkaryl, alkenyl, ammonium, primary, secondary, tertiary, quaternary alkyl and/or aryl ammonium, an alkali metal, an alkaline earth metal, a metal of the third and fourth main group and the second, fourth and eight subgroup or a metal of the lanthanoid group. The invention also relates to methods for producing same and to the uses of said compounds.

8 Claims, No Drawings

ALKYLPHOSPHONOUS ACIDS, SALTS AND ESTERS, METHODS FOR THE PRODUCTION THEREOF, AND USE OF THE SAME

The invention relates to alkylphosphonous acids, alkylphosphonous salts, and alkylphosphonous esters, their use, and processes for their production.

The available prior art contains only partial disclosure of alkylphosphonous acids such as those complying with the formula (I)

$$A\text{-}P(=O)(OX)\text{-}H \quad (I)$$

since these acids have hitherto been unobtainable or obtainable only with great difficulty. Many theoretically conceivable alkylphosphonous acids have never been prepared.

The prior art says that selective preparation of alkylphosphonous acids starting from phosphinic acids by a free-radical-initiated route, examples being the free-radical addition reaction of olefins, the addition reaction of Michael systems, or the addition reaction of alkyl halides, has very inadequate success or is only successful by way of circuitous routes, e.g. by way of a route involving protective groups; the yields are extremely low.

The only transition-metal-catalyzed preparation process known uses long-chain and, respectively, aryl-substituted olefins (Montchamp, J.-L. et. al., J. Am. Chem. Soc. 2002, 124, 9386-9387, and also Org. Lett. 2004, 6, 3805-3808, and 2006, 8, 4169-4171; and also J. Org. Chem. 2005, 70, 4064-4072). The reaction is moreover carried out with an excess of phosphorus-containing component in order to arrive at the desired monoalkylated product. Compounds hitherto found to be suitable are only phosphinic acid, methyl-, ethyl-, and butylphosphinic esters, and the anilinium salt of phosphinic acid.

The invention is therefore based on the object of providing alkylphosphonous acids and processes for their preparation, where these permit production of the desired alkylphosphonous acids in a particularly simple and cost-effective manner, and also in appropriately high yields. A particular intention is to permit reproducible production of alkylphosphonous acids having short side chains, with good yields.

The invention therefore provides alkylphosphonous acids, alkylphosphonous salts, and alkylphosphonous esters of the formula (I)

$$A\text{-}P(=O)(OX)\text{-}H \quad (I)$$

in which
A is $C_2$-$C_{20}$-alkyl, $C_2$-$C_{20}$-alkylene, $C_8$-$C_{20}$-alkaryl, optionally substituted, and
X is H, alkyl, aryl, alkylaryl, alkenyl, substituted alkyl, aryl, alkaryl, alkenyl, ammonium, or primary, secondary, tertiary, or quaternary alkyl- or arylammonium, alkali metal, alkaline earth metal, metal of the third or fourth main group or of the second, fourth or eighth transition group, or a metal of the lanthanoid group.

The compounds here are preferably ethyl-, n-propyl-, isopropyl-, n-butyl-, isobutyl-, n-pentyl-, isopentyl-, n-hexyl-, isohexyl-, 2-phenylethyl-, 1-phenylethyl-, 3-phenylpropyl-, 2-phenylpropyl-, 2-hydroxyethyl-, 3-hydroxypropyl-, 2-carboxyethyl-, 3-carboxypropyl-, 2-acetatoethyl-, 3-acetatopropyl-, 2-butyratoethyl-, 3-butyratopropyl-, 2-ethyloxyethyl-, 3-ethyloxypropyl-, 2-propyloxyethyl-, 3-propyloxypropyl-, 2-butyloxyethyl-, 3-butyloxypropyl-, 3-carboxypropyl-, 2-aminoethyl-, and/or 3-aminopropylphosphonous acid, salts thereof, esters thereof, and/or a mixture of these.

The alkylphosphonous salts are preferably alkali metal salts, alkaline earth metal salts, salts of the elements of the third or fourth main group or of the second, fourth, or eighth transition group, or of the lanthanoid group, ammonium salts, or primary, secondary, tertiary, or quaternary alkyl- or arylammonium salts.

The alkylphosphonous esters are preferably alkyl, hydroxyalkyl, alkylaryl, aryl, or alkenyl esters.

It is particularly preferable that these are the methyl, ethyl, propyl, butyl, ethylene glycol, propylene glycol, benzyl, phenyl, vinyl, and/or allyl esters.

The present object is also achieved via a process for the production of alkylphosphonous acids, of alkylphosphonous salts, and of alkylphosphonous esters, which comprises reacting a source of phosphinic acid with olefins in the presence of a catalyst.

It is preferable that the source of phosphinic acid is phosphinic acid (hypophosphorous acid $H_3PO_2$), a salt of phosphinic acid, an ester of phosphinic acid, or a mixture of these.

One process of the invention for the production of alkylphosphonous acids, of alkylphosphonous salts, and of alkylphosphonous esters, is one wherein
a) a source of phosphinic acid is reacted with olefins in the presence of a catalyst,
b) solvent and/or olefin is optionally removed,
c) catalyst, catalyst system, transition metal, and/or transition metal compound is removed,
d) ligand and/or complexing agent is removed, and
e) auxiliary and/or olefin is removed.

Another process of the invention for the production of alkylphosphonous acids, of alkylphosphonous salts, and of alkylphosphonous esters, is one wherein
a) a source of phosphinic acid is reacted with olefins in the presence of a catalyst, and
b) insoluble product is removed by filtration.

Another process of the invention for the production of alkylphosphonous acids, of alkylphosphonous salts, and of alkylphosphonous esters, is one wherein
a) a source of phosphinic acid is reacted with olefins in the presence of a catalyst,
b) optionally catalyst is removed,
c) ligand and/or complexing agent is removed, and
d) solvent is removed.

Another process of the invention for the production of alkylphosphonous acids, of alkylphosphonous salts, and of alkylphosphonous esters, is one wherein
a) a source of phosphinic acid is reacted with olefins in the presence of a catalyst,
b) optionally catalyst is removed,
c) ligand and/or complexing agent is removed, and
d) solvent is removed,
e) at least 90% of complexing agent and/or ligand and/or catalyst that has been removed is returned to step a).

It is preferable that the salt of phosphinic acid is an alkali metal salt, an alkaline earth metal salt, a salt of the elements of the third or fourth main group and of the second, fourth, or eighth transition group, or of the lanthanoid group, an ammonium salt, or a primary, secondary, tertiary, or quaternary alkyl- or arylammonium salt.

It is preferable that the esters of phosphinic acid are the alkyl, hydroxyalkyl, alkylaryl, aryl, and/or alkenyl esters.

It is preferable that the olefins in the process of the invention comply with the general formula (II)

$$R^1R^2C=CR^3R^4 \quad (II)$$

in which $R^1$ to $R^4$ are identical or different and are hydrogen, an alkyl group having from 1 to 18 carbon atoms, and/or an alkenyl group having from 2 to 18 carbon atoms, and/or are an aryl group having from 8 to 18 carbon atoms, and/or functional groups such as carbonyl, aldehyde, carboxy, hydroxy, sulfonic acid, nitrile, cyano, and/or epoxy groups; or are primary, secondary, and/or tertiary amino groups, and/or ester or ether groups.

It is preferable that the olefins are ethylene, 1-propylene, 1-butene, 1-pentene, 1-hexene, styrene, allylamine, allyl alcohol, allyl alcohol ether and vinyl alcohol ether, acrylic acid, acrylic ester, vinyl acetate, and/or 1,3-butadiene.

It is preferable that the catalysts are transition metals and/or transition metal compounds and/or catalyst systems composed of a transition metal and/or of a transition metal compound, and of at least one ligand.

It is preferable that the catalyst system is formed via reaction of a transition metal and/or of a transition metal compound, and of at least one ligand.

It is preferable that the transition metals and/or transition metal compounds are those of the seventh and eighth transition group.

It is particularly preferable that the transition metals and/or transition metal compounds involve rhodium, nickel, palladium, and/or platinum.

The invention also provides the use of alkylphosphonous acids, of alkylphosphonous salts, and of alkylphosphonous esters as claimed in one or more of claims 1 to 6, and/or of alkylphosphonous acids, of alkylphosphonous salts, and of alkylphosphonous esters produced by a process of the invention as intermediate product for further syntheses,
as binder,
as crosslinking agent or accelerator in the hardening of epoxy resins, of polyurethanes, or of unsaturated polyester resins,
as polymer stabilizers,
as plant-protection agents,
as therapeutic agent or additive in therapeutic agents for humans and animals,
as sequestering agent,
as petroleum additive,
as corrosion-protection agent,
in laundry-detergent applications and cleaning-product applications,
in electronics applications.

The invention also provides the use of alkylphosphonous acids, of alkylphosphonous salts, and of alkylphosphonous esters, as claimed in one or more of claims 1 to 6, and/or of alkylphosphonous acids, of alkylphosphonous salts, and of alkylphosphonous esters produced by a process of the invention, as flame retardant, in particular flame retardant for clearcoats and intumescent coatings, flame retardant for wood and other cellulose-containing products, or as reactive and/or non-reactive flame retardant for polymers, for the production of flame-retardant polymer molding compositions, for the production of flame-retardant polymer moldings, and/or for providing flame retardancy to polyester and to unblended or blended cellulose textiles via impregnation.

The invention equally provides a flame-retardant thermoplastic or thermoset polymer molding composition, comprising from 0.5 to 45% by weight of alkylphosphonous acid, of alkylphosphonous salts, or of alkylphosphonous ester, as claimed in at least one of claims 1 to 6, and/or of alkylphosphonous acids, of alkylphosphonous salts, or of alkylphosphonous esters produced by a process of the invention, from 0.5 to 95% by weight of thermoplastic or thermoset polymer, or a mixture of the same, from 0 to 55% by weight of additives, and from 0 to 55% by weight of filler or reinforcing materials, where the entirety of the components is 100% by weight.

Finally, the invention provides flame-retardant thermoplastic or thermoset polymer moldings, polymer films, polymer filaments, and polymer fibers, comprising from 0.5 to 45% by weight of alkylphosphonous acid, of alkylphosphonous salts, or of alkylphosphonous ester, as claimed in at least one of claims 1 to 6, and/or of alkylphosphonous acids, of alkylphosphonous salts, or of alkylphosphonous esters produced by a process of the invention, from 0.5 to 95% by weight of thermoplastic or thermoset polymer, or a mixture of the same, from 0 to 55% by weight of additives, and from 0 to 55% by weight of filler or reinforcing materials, where the entirety of the components is 100% by weight.

Another preferred meaning of A is $C_2$-$C_6$-alkyl.

Another preferred meaning of A is $C_2$-$C_8$-alkyl or $C_2$-$C_8$-alkylene.

Preference is also given to $C_8$-$C_{16}$-alkaryl, in particular $C_8$-$C_{11}$-alkaryl.

It is preferable that the moiety A bears heteroatoms and/or has substitution by functional groups.

It is preferable that the functional groups are carbonyl, aldehyde, carboxy, hydroxy, sulfonic acid, nitrile, cyano, and/or epoxy groups; or are primary, secondary, and/or tertiary amino groups, and/or ester or ether groups.

It is preferable that the functionalized alkyl groups are 2-hydroxyethyl, 3-hydroxypropyl, 2-carboxyethyl, 3-carboxypropyl, 2-aminoethyl, or 3-aminopropyl.

The moiety A can derive from an olefin of the general formula $$R^1R^2C\!=\!CR^3R^4 \tag{II}$$

in which $R^1$ to $R^4$ can be identical or different, and are hydrogen, alkyl groups having from 1 to 18 carbon atoms, alkenyl groups having from 2 to 18 carbon atoms, and/or aryl groups having from 8 to 18 carbon atoms, and/or functional groups such as carbonyl, aldehyde, carboxy, hydroxy, sulfonic acid, nitrile, cyano, and/or epoxy groups; or are primary, secondary, and/or tertiary amino groups, and/or are ester or ether groups.

It is preferable that the olefins are linear or branched α-olefins.

It is preferable that the olefins are cyclic, or open-chain olefins having an internal double bond, cyclic or open-chain dienes and/or polyenes.

It is preferable that the olefins have from 2 to 20 carbon atoms.

It is particularly preferable that the olefins have from 2 to 6 carbon atoms.

It is preferable that the olefins bear heteroatoms and/or a functional group.

It is preferable that the functional groups are carbonyl, aldehyde, carboxy, hydroxy, sulfonic acid, nitrile, cyano, and/or epoxy groups; or are primary, secondary, and/or tertiary amino groups, and/or ester or ether groups.

Preferred olefins for the process described are ethylene, propylene, 1-butene, 3-methylbutene, 1-pentene, 4-methyl-1-pentene, 1-hexene, 1-heptene, 1-octenes, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, styrene, methylstyrene, 2-butene, cyclohexene, norbornene, butadiene, 1,5-hexadiene, acrylic acid and its methyl, ethyl, and butyl esters, methacrylic acid and its methyl, ethyl, and butyl esters, acrylonitrile, vinyl acetate, vinyl butyrate, vinyl benzoate, vinyl ethyl ether, vinyl butyl ether, divinyl ether, 2-vinyl-1,3-dioxolane, methyl 3-butenoate, methyl 4-pentenoate, allyl alcohol, allyl acetate, allyl butyrate, allyl ethyl ether, allyl butyl ether, allylamine.

It is particularly preferable that the olefins are ethylene, 1-propylene, 1-butene, 2-butene, 1-pentene, 1-hexene, styrene, allylamine, allyl alcohol, vinyl acetate, acrylic acid, and methyl, ethyl, and butyl esters.

It is particularly preferable that the salts of phosphinic acids are the lithium, sodium, potassium, magnesium, calcium, barium, aluminum, lead, titanium, iron, zinc, ammonium, anilinium, trimethylammonium, triethylammonium, tripropylammonium, tributylammonium, tetramethylammonium, tetraethylammonium, tetrapropylammonium, tetrabutylammonium, trimethylsilylammonium, and/or N-ethylpiperidine salts.

It is particularly preferable that the salt of phosphinic acid is the lithium, sodium, potassium, magnesium, calcium, barium, aluminum, lead, titanium, iron, zinc, ammonium, anilinium, trimethylammonium, triethylammonium, tripropylammonium, tributylammonium, tetramethylammonium, tetraethylammonium, tetrapropylammonium, tetrabutylammonium, trimethylsilylammonium, and/or N-ethylpiperidine salt.

It is preferable that the esters of phosphinic acid are the methyl, ethyl, propyl, butyl, ethylene glycol, propylene glycol, benzyl, phenyl, vinyl, and/or allyl esters.

It is preferable that the catalyst system is composed of a transition metal and/or of a transition metal compound, and of at least one ligand.

It is preferable that the transition metals are elements of the seventh and eighth transition group (according to modern nomenclature, a metal of group 7, 8, 9, or 10), examples being rhenium, ruthenium, cobalt, rhodium, iridium, nickel, palladium, and platinum.

It is preferable that the source used for the transition metals and transition metal compounds comprises the salts of these metals. Suitable salts include simple salts of mineral acids, examples being the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate, and sulfonate, e.g. methanesulfonate, chlorosulfonate, fluorosulfonate, trifluoromethane-sulfonate, benzenesulfonate, naphthylsulfonate, toluenesulfonate, tert-butylsulfonate, 2-hydroxypropanesulfonate, and sulfonated ion-exchanger resins; and/or organic salts, e.g. acetylacetonates and salts of a carboxylic acid having up to 20 carbon atoms, e.g. formate, acetate, propionate, butyrate, oxalate, stearate, and citrate, including those of halogenated carboxylic acids having up to 20 carbon atoms, e.g. trifluoroacetate and trichloroacetate. A further source of the transition metals and transition metal compounds is provided by salts of the transition metals with tetraphenylborate anions and with halogenated tetraphenylborate anions, e.g. perfluorophenylborate.

Suitable salts equally include double salts and complex salts composed of one or more transition metal ions and, independently of one another, include one or more alkali metal, alkaline earth metal, ammonium, organic ammonium, phosphonium and organic phosphonium ions and, independently of one another, one or more abovementioned anions. Examples of suitable double salts are ammonium hexachloropalladate and ammonium tetrachloropalladate.

Other suitable sources of the metal salts are complexes of these. Complexes of the metal salts are composed of the metal salts and of one or more complexing agents. Examples of suitable complexing agents are olefins, diolefins, nitriles, dinitriles, carbon monoxide, phosphines, and diphosphines.

It is preferable that the source of the transition metals is the transition metal in the form of element and/or a transition metal compound in its zero-valency state.

It is preferable that the transition metal is used in metallic form.

Another preference is that the transition metal is used in the form of an alloy with further metals.

It is particularly preferable that the transition metal is used in the form of alloy with at least one additional element of the group of boron, zirconium, tantalum, tungsten, rhenium, cobalt, iridium, nickel, palladium, platinum, and/or gold.

It is preferable that the transition metal content in the alloy used is from 45 to 99.95%.

It is preferable that the transition metal is used in microdisperse form (particle size 0.1 mm-100 μm).

It is preferable that the transition metal is used in a form supported on a metal oxide, e.g. aluminum oxide, silicon dioxide, titanium dioxide, zirconium dioxide, zinc oxide, nickel oxide, vanadium oxide, chromium oxide, magnesium oxide, or on a metal carbonate, e.g. barium carbonate, calcium carbonate, strontium carbonate, or on a metal sulfate, e.g. barium sulfate, calcium sulfate, strontium sulfate, or on a metal phosphate, e.g. aluminum phosphate, vanadium phosphate, or on a metal carbide, e.g. silicon carbide, or on a metal aluminate, e.g. calcium aluminate, or on a metal silicate, e.g. aluminum silicate, or on chalks, zeolites, bentonite, montmorillonite, or hectorite, or on a metal nitride, or on carbon, activated charcoal, mullite, bauxite, antimonite, scheelite, perovskite, hydrotalcite, or on heteropolyanions, and/or polyethyleneimine/silicon dioxide.

It is preferable that the transition metal is used in the form of complex. Complexes of the element are composed of the element and of one or more complexing agents. Suitable complexing agents are olefins, diolefins, nitriles, dinitriles, carbon monoxide, phosphines, and/or diphosphines, e.g. triphenylphosphine, dibenzylideneacetone, or styrene, and can be in the form supported on the abovementioned support materials.

Examples of suitable sources of transition metals and transition metal compounds are palladium, 1,4-bis(diphenylphosphino)butanepalladium(II) chloride, 2-(T-di-tert-butylphosphine)biphenylpalladium(II) acetates, ammonium hexachloropalladate(IV), ammonium tetrachloropalladate (II), bis(acetonitrile)dichloropalladium(II), bis(benzonitrile) palladium(II) chloride, bis(dibenzylideneacetone)palladium (0), bis(triphenylphosphine)palladium(II) diacetate, bis (triphenylphosphine)palladium(II) dichloride, bromo(tri-tert-butylphosphine)palladium(I) dimer, (ethylenediamine)-palladium(II) chloride, palladium black, palladium hydroxide on activated charcoal, palladium hydroxide on carbon, palladium(II) acetate, palladium(II) acetylacetonate, palladium(II) bromides, palladium(II) chlorides, palladium (II) chloride, diacetonitrile complex, palladium(II) cyanide, palladium(II) hexafluoroacetylacetonate, palladium(II) iodide, palladium(II) nitrate, palladium(II) oxide, palladium (II) thiosulfate sodium salt, palladium(II) propionate, palladium(II) sulfate, palladium(II) sulfides, palladium(II) tetrafluoroborate, tetraacetonitrile complex, palladium(II) trifluoroacetate, palladium on alumina, palladium on barium carbonate, palladium on barium sulfate, palladium on calcium carbonate, palladium on carbon, palladium on activated charcoal, palladium on strontium carbonate, sodium tetrachloropalladate(II), tetrakis(acetonitrile)palladium(II) tetrafluoroborate, tetrakis(triphenylphosphine)palladium(0), tetrakis(tricyclohexyl-phosphine)palladium, polymer-bound, (2-methylallyl)palladium(II) chloride dimer, N-methylimidazoliumpalladium(II), platinum/palladium/gold alloy, potassium hexachloropalladate, potassium tetrachloropalladate, tris(dibenzylideneacetone)dipalladium chloroform complex, [1,2,3,4-tetrakis(methoxycarbonyl)-1,3-butadiene-1,4-diyl]palladium(II), 1,2-bis(phenylsulfinyl)ethanepalladium(II) acetate, (1,3-bis(2,6-diisopropylphenyl)imidazolidene)(3-chloropyridyl)palladium(II) dichloride, 2-[bis(triphenylphosphine)palladium(II) bromide]benzyl alcohol, 2'-(dimethylamino)-2-biphenylpalladium(II) chloride dinorbornylphosphine complex, 2-(dimethylaminomethyl)ferrocen-1-ylpalladium(II) chloride, dinorbornylphosphine complex, ([2S,3S]-bis[diphenylphosphino]butane)(η3-allyl)palladium(II) perchlorate, bis[1,2-bis(diphenylphosphino)ethane]palladium(0), bis(3,5,3',5'-dimethoxydibenzylideneacetone)palladium(0), bis[(diphenylphosphanyl)methyl]aminepalladium(II) acetate, polymer-bound, bis[(diphenylphosphanyl)methyl]aminepalladium(II) dichloride, polymer-bound, bis(tri-tert-butylphosphine)palladium(0), bromo(N-succinimidyl)bis(triphenylphosphine)palladium(II), cis-dichlorobis(dimethylphenylphosphine)palladium(II), diacetobis(triphenylphosphine)palladium(II), polymer-bound, dichloro(1,10-phenanthroline)palladium(II), bis(1,5-cyclooctadiene)palladium(0), dichloro(1,5-cyclooctadiene)palladium(II), dichloro(N,N,N',N'-tetramethylethylenediamine)palladium(II), dichlorobis(methyldiphenylphosphine)palladium(II), dichlorobis(tri-o-tolylphosphine)palladium(II), dichlorobis(tricyclohexylphosphine)palladium(II), dichlorobis(triethylphosphine)palladium(II), dichlorobis(triphenylphosphine)palladium(II), polymer-bound, meso-tetraphenyltetrabenzoporphine palladium complex, [(R)(+)-2,2'-bis(diphenylphosphino)-1,1'-binaphthyl]palladium(II) chloride, tetrakis(methyldiphenylphosphine)palladium(0), trans-benzyl(chloro)bis(triphenylphosphine)palladium(II), trans-dibromobis(triphenylphosphine)palladium(II), tris(3,3',3''-phosphineidyntris(benzene-sulfonato)palladium(0) nonasodium salt, 1,3-bis(2,4,6-trimethylphenyl)imidazol-2-ylidene(1,4-naphthoquinone)palladium(0) dimer, 1,3-bis(2,6-diisopropylphenyl)imidazol-2-ylidene(1,4-naphthoquinone)palladium(0) dimer, 2,3,7,8,12,13,17,18-octaethyl-21H,23H-porphinepalladium(II), 2-[bis(2,4-di-tert-butylphenoxy)phosphinooxy)-3,5-di(tert-butyl)phenylpalladium(II) chloride dimer, 5,10,15,20-tetrakis(pentafluorophenyl)-21H,23H-porphinepalladium(II), allyl[1,3-bis(2,6-diisopropylphenyl)imidazol-2-ylidene]palladium(II) chloride, allyl[1,3-bis(mesityl)imidazol-2-ylidene]palladium chloride, bis[tris(3-(1H,1H,2H,2H-perfluorodecyl)phenyl)phosphine]palladium(II) dichloride, bis[tris(3-(heptadecafluorooctyl)phenyl)phosphine]palladium(II) dichloride, bis[tris(4-(1H,1H,2H,2H-perfluorodecyl)phenyl)phosphine]palladium(II) dichloride, bis[tris(4-(heptadecafluorooctyl)phenyl)phosphine]palladium(II) dichloride, bromo[(2-(hydroxy-κO)methypphenylmethyl-κC](triphenylphosphine)palladium(II), chloro(η2-P,C-tris(2,4-di-tert-butylphenyl)phosphite)(tricyclohexylphosphine)palladium(II), di-µ-chlorobis[5-hydroxy-2-[1-(hydroxyimino-κN)ethyl]phenyl-κC]palladium(II) dimer, di-µ-chlorobis[5-chloro-2-[(4-chlorophenyl)(hydroxyimino-kn)methyl]phenyl-kc]palladium dimer, dichloro[(S)—N,N-dimethyl-1-[(R)-2-(diphenylphosphino)ferrocenyl]-ethylamine]palladium(II), [1,1'-bis(diphenylphosphino)ferrocene]dichloropalladium(II), [1,2-bis(diphenylphosphino)ethane]dichloropalladium(II), (2,2'-bipyridine)dichloropalladium(II), allylpalladium(II) chloride dimer, (bicyclo[2.2.1]hepta-2,5-diene)dichloropalladium(II), bis(di-tert-butyl(4-dimethylaminophenyl)phosphine)dichloropalladium(II), di(acetato)dicyclohexylphenylphosphinepalladium(II), polymer-bound, di-µ-chlorobis[2-[(dimethylamino)methyl]phenyl-C,N]dipalladium(II), diaminedibromopalladium(II), diaminediiodopalladium(II), tetraaminepalladium(II) acetate, tetraaminepalladium(II) bromide, tetraaminepalladium(II) chloride, tetraaminepalladium(II) nitrate, tetraaminepalladium(II) tetrachloropalladate(II), trans-diaminedichloropalladium(II), trans-diaminedinitropalladium(II), tris(dibenzylideneacetone)dipalladium(0), nickel, 1,3-bis(diphenylphosphino)propanenickel(II) chloride, 2,3,7,8,12,13,17,18-octaethyl-21H,23H-porphinenickel(II), 5,10,15,20-tetraphenyl-21H,23H-porphinenickel(II), allyl(cyclopentadienyl)nickel(II), allylnickel(II) chloride dimer, aluminum-nickel alloy, bis(tert-butylisocyanide)palladium(II) chloride, ammonium nickel(II) sulfate, bis(1,5-cyclooctadiene)nickel(0), bis[5-[[4-(dimethylamino)phenyl]imino]-8(5H)-quinolinone]nickel(II), bis(cyclopentadienyl)nickel(II), bis(methylcyclopentadienyl)nickel(II), bis(pentamethylcyclopentadienyl)nickel(II), bis(tetramethylcyclopentadienyl)nickel(II), bis(triphenylphosphine)dicarbonylnickel, bis(triphenylphosphine)nickel(II) dichloride, chloro(cyclopentadienyl)(triphenylphosphine)nickel(II), dibromobis(tributylphosphine)nickel(II), dibromobis(triphenylphosphine)nickel(II), dichloro-bis(tributylphosphine)nickel(II), dichlorobis(trimethylphosphine)nickel(II), iron-nickel alloy, nickel carbonate, nickel(II)1,4,8,11,15,18,22,25-octabutoxy-29H,31H-phthalocyanine, nickel(II) acetate, nickel(II) acetylacetonate, nickel(II) bromide, nickel(II) bromide 2-methoxyethyl ether complex, nickel(II) bromide ethylene glycol dimethyl ether complex, nickel(II) carbonate, nickel(II) chloride, nickel(II) fluoride, nickel(II) hexafluoroacetylacetonate, nickel(II) iodide, nickel(II) nitrate, nickel(II) peroxide, nickel(II) phthalocyaninetetrasulfonic acid tetrasodium salt, nickel(II) stearate, nickel(II) sulfate, nickel(II) tetrakis(4-cumylphenoxy)phthalocyanine, nickel on silica, nickel on silica/alumina, 1,2-dimethoxyethanenickel dibromide, nickel oxide on silica, nickel phosphide, nickel sulfide, potassium hexafluoronickelate(IV), potassium tetracyanonickelate(II), Raney® nickel, tetrakis(triphenylphosphine)nickel(0), tetrakis(triphenyl phosphite)nickel(0), nickel boride, nickel chromium oxide, nickel cobalt oxide, nickel(II)2,11,20,29-tetra-tert-butyl-2,3-naphthalocyanine, nickel(II)2,9,16,23-tetraphenoxy-29H,31H-phthalocyanine, nickel(II) 2-ethylhexanoate, nickel(II)5,9,14,18,23,27,32,36-octabutoxy-2,3-naphthalocyanine, nickel(II) bis(2,2,6,6-tetramethyl-3,5-heptanedionate), nickel(II) carbonate hydroxide, nickel(II) cyclohexanebutyrate, nickel(II) hydroxide, nickel(II) molybdate, nickel(II) octanoate, nickel(II) oxalate, nickel(II) oxide, nickel(II) perchlorate, nickel(II) phthalocyanine, nickel(II) sulfamate, nickel(II) sulfate, nickel zinc iron oxide, etioporphyrin I nickel, lanthanoid-nickel alloy, $LaNi_{4.5}Co_{0.5}$, lanthanoid-nickel alloy, $LaNi_5$, mixed metal-nickel alloy, (Ce, La, Nd, Pr)$Ni_5$, potassium nickel(IV) paraperiodate, zirconium-nickel alloy, bis(ethylcyclopentadienyl)nickel(II), bis(ethylenediamine)nickel(II) chloride, bis(N,N'-diisopropylacetamidinato)nickel(II), tris(ethylenediamine)nickel(II) chloride, bis(N,N-dimethyl-N'-5H-pyrido[2,3-a]phenothiazin-5-ylidene-1,4-phenylenediamine)nickel(II) diperchlorate, bis(1,3-diamino-2-propanol)nickel(II) thiocyanate, bis(N,N-diethylethylenediamine)nickel(II) thiocyanate, tris(ethylenediamine)nickel(II) chloride, tris(ethylenediamine)nickel(II) sulfate, 2,2'-thiobis(4-tert-octylphenolato)-N-butylaminenickel(II), [1,1'-bis(diphenylphosphino)ferrocene]dichloronickel(II), [1,2-bis(diphenylphosphino)ethane]dichloronickel(II), chloro (ethylcyclopentadienyl)-triphenylphosphinenickel(II), dilithium tetrabromonickelate(II), hexaaminenickel(II) bromide, N,N'-bis(salicylidene)ethylenediaminonickel(II), potassium tetracyanonickelate(II), cis-diamineplatinum(II) dichloride, cis-dichlorobis(diethyl sulfide)platinum(II), cis-dichlorobis(pyridine)platinum(II), cis-dichlorobis(triethylphosphine)platinum(II), cis-dichlorobis(triphenylphosphine)platinum(II), dibromo(1,5-cyclooctadiene)platinum (II), dichloro(1,10-phenanthroline)platinum(II), dichloro(1, 2-diaminocyclohexane)platinum(II), dichloro(1,5-cyclooctadiene)platinum(II), dichloro(ethylenediamine) platinum(II), dichlorobis(ethylenediamine)platinum(II), ethylenebis(triphenylphosphine)platinum(0), (N,N,N'-trimethylethylenediamine)platinum(III) chloride, polymer-bound, platinum, platinum(0)-1,3-divinyl-1,1,3,3-tetramethyldisiloxane, platinum(0)-2,4,6,8-tetramethyl-2,4,6,8-tetravinylcyclotetrasiloxane, platinum black, platinum(II) acetylacetonate, platinum(II) bromide, platinum(II) chloride, platinum(II) iodide, platinum(IV) chloride, platinum(IV) oxide, platinum on activated charcoal, platinum on alumina, platinum on carbon, platinum on silica, potassium hexachloroplatinate(IV), tetrakis(triphenylphosphine)platinum(0), trans-dichlorobis(triethylphosphine)platinum(II), trans-dichlorobis(triphenylphosphine)platinum(II), ammonium hexachloroplatinate(IV), ammonium tetrachloroplatinate (II), platinum(II) cyanide, platinum-iridium alloy (70:30), platinum(IV) sulfide, platinumoctaethylporphyrine, platinum-palladium-gold alloy, platinum-rhodium alloy, sodium hexachloroplatinate(IV), trans-platinum(II) diamine dichloride, potassium tetrachloroplatinate(II), potassium tetracyanoplatinate(II), chloro(2,2':6',2''-terpyridine)platinum(II) chloride, dichloro(2,2':6',2''-terpyridine)platinum(II), oxaliplatinum, trans-dichlorobis(diethyl sulfide)platinum(II), trimethyl(methylcyclopentadienyl)platinum(IV), carboplatinum, (+)-trans-dichloro(ethylene)(ALPHA-methylphenethylamine)platinum(II), (1,5-cyclooctadiene) dimethylplatinum(II), (2,2'-bipyridine)dichloroplatinum(II), chloroplatinic acid, cis-bis(acetonitrile)dichloroplatinum (II), cis-bis(benzonitrile)dichloroplatinum(II), cis-diamminetetrachloroplatinum(IV), diaminedinitritoplatinum(II), potassium trichloro(ethylene)platinate(II), sodium hexahydroxyplatinate(IV), tetraamineplatinum(II) chloride, tetraamineplatinum(II) hydroxide, tetraamineplatinum(II) nitrate, tetraamineplatinum(II) tetrachloroplatinate(II), tetrabutylammonium hexachloroplatinate(IV), rhodium acetate dimer, rhodium chloride, rhodium bromide, rhodium iodide, rhodium acetylacetonate, acetylacetonatobis(ethylene) rhodium, chlorobis(ethylene)rhodium dimer, dicarbonyl (acetylacetonato)rhodium, hexarhodiumhexadecacarbonyl, chloro(1,5-cyclooctadiene)rhodium dimer, chloro(norbornadiene)rhodium dimer, chloro(1,5-hexadiene)rhodium dimer, chlorocarbonylbis(triphenylphosphine), hydridocarbonyltris(triphenylphosphine)rhodium, chlorotris(triphenylphosphine)rhodium, bromotris(triphenylphosphine)rhodium, iodotris(triphenylphosphine)rhodium, chlorocarbonylbis(trimethyl phosphite)rhodium, bromotris(triphenylphosphine)rhodium, chloro(1,5-cyclooctadienyl)(triphenylphosphine)rhodium, trichlorotris(pyridine)rhodium and/or bis(1,5-cyclooctadiene)rhodium(I) tetrafluoroborate.

It is preferable that the ligands are phosphines of the formula (III)

$$PR^5_3 \qquad (III)$$

in which the moieties $R^5$, independently of one another, are hydrogen, straight-chain, branched or cyclic $C_1$-$C_{20}$ alkyl, $C_1$-$C_{20}$ alkylaryl, $C_2$-$C_{20}$ alkenyl, $C_2$-$C_{20}$ alkynyl, $C_1$-$C_{20}$ carboxylate, $C_1$-$C_{20}$ alkoxy, $C_1$-$C_{20}$ alkenyloxy, $C_1$-$C_{20}$ alkynyloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, silyl, or derivatives of these, and/or phenyl substituted by at least one $R^6$, or naphthyl substituted by at least one $R^6$. $R^6$ is mutually independently hydrogen, fluorine, chlorine, bromine, iodine, $NH_2$, nitro, hydroxy, cyano, formyl, straight-chain, branched or cyclic $C_1$-$C_{20}$ alkyl, $C_1$-$C_{20}$ alkoxy, $HN(C_1$-$C_{20}$ alkyl), $N(C_1$-$C_{20}$ alkyl)$_2$, —$CO_2$—($C_1$-$C_{20}$ alkyl), —$CON(C_1$-$C_{20}$ alkyl)$_2$, —$OCO(C_1$-$C_{20}$ alkyl), $NHCO(C_1$-$C_{20}$ alkyl), $C_1$-$C_{20}$ acyl, —$SO_3M$, —$SO_2N(R^7)M$, —$CO_2M$, —$PO_3M_2$, —$AsO_3M_2$, —$SiO_2M$, —$C(CF_3)_2OM$ (M=H, Li, Na, K), where $R^7$ can be hydrogen, fluorine, chlorine, bromine, iodine, straight-chain, branched or cyclic $C_1$-$C_{20}$ alkyl, $C_2$-$C_{20}$ alkenyl, $C_2$-$C_{20}$ alkynyl, $C_1$-$C_{20}$ carboxylate, $C_1$-$C_{20}$ alkoxy, $C_1$-$C_{20}$ alkenyloxy, $C_1$-$C_{20}$ alkynyloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, silyl, and derivatives of these, aryl, $C_1$-$C_{20}$ arylalkyl, $C_1$-$C_{20}$ alkylaryl, phenyl, and/or biphenyl.

It is preferable that all of the $R^5$ groups are identical.

Examples of suitable phosphines (III) are trimethylphosphine, triethylphosphine, tripropylphosphine, triisopropylphosphine, tributylphosphine, triisobutylphosphine, triisopentylphosphine, trihexylphosphine, tricyclohexylphosphine, trioctylphosphine, tridecylphosphine, triphenylphosphine, diphenylmethylphosphine, phenyldimethylphosphine, tri(o-tolyl)phosphine, tri(p-tolyl) phosphine, ethyldiphenylphosphine, dicyclohexylphenylphosphine, 2-pyridyldiphenylphosphine, bis(6-methyl-2-pyridyl)-phenylphosphine, trip-chlorophenyl)phosphine, trip-methoxyphenyl)phosphine, diphenyl(2-sulfonatophenyl)phosphine sodium salt, diphenyl(2-sulfonatophenyl)phosphine potassium salt, diphenyl(2-sulfonatophenyl)phosphine ammonium salt, diphenyl(3-sulfonatophenyl)phosphine sodium salt, diphenyl(3-sulfonatophenyl)phosphine potassium salt, diphenyl(3-sulfonatophenyl)phosphine ammonium salt, bis(4,6-dimethyl-3-sulfonatophenyl)(2,4-dimethylphenyl) phosphine disodium salt, bis(4,6-dimethyl-3-sulfonatophenyl)(2,4-dimethylphenyl)phosphine dipotassium salt, bis(4,6-dimethyl-3-sulfonatophenyl)(2,4-dimethylphenyl)phosphine diammonium salt, bis(3-sulfonatophenyl)phenylphosphine disodium salt, bis(3-sulfonatophenyl)phenylphosphine dipotassium salt, bis(3-sulfonatophenyl)phenylphosphine diammonium salt, tris(4, 6-dimethyl-3-sulfonatophenyl)phosphine trisodium salt, tris (4,6-dimethyl-3-sulfonatophenyl)phosphine tripotassium salt, tris(4,6-dimethyl-3-sulfonatophenyl)phosphine triammonium salt, tris(2-sulfonatophenyl)phosphine trisodium salt, tris(2-sulfonatophenyl)phosphine tripotassium salt, tris (2-sulfonatophenyl)phosphine triammonium salt, tris(3-sulfonatophenyl)phosphine trisodium salt, tris(3-sulfonatophenyl)phosphine tripotassium salt, tris(3-sulfonatophenyl) phosphine triammonium salt, 2-bis(diphenylphosphinoethyl) trimethylammoniumiodide, 2'-dicyclohexylphosphino-2,6-dimethoxy-3-sulfonato-1,1'-biphenyl sodium salt, dimethyl phosphite, and/or triperyl phosphite.

It is particularly preferable that the ligands are bidentate ligands of the general formula $$R^5_2M\text{-}X\text{-}MR^5_2 \qquad (IV).$$

In this formula, M represent, independently of one another, N, P, As, or Sb.

It is preferable that the two M are identical and it is particularly preferably that M is a phosphorus atom.

Each group $R^5$ represents mutually independently the moieties described by formula III. It is preferable that all of the groups $R^5$ are identical.

X is preferably a bivalent bridging group which contains at least 1 bridging atom, preference being given to the presence of from 2 to 6 bridging atoms.

Bridging atoms can be selected from C atoms, N atoms, O atoms, Si atoms, and S atoms. It is preferable that X is an organic bridging group which contains at least one carbon atom. It is preferable that X is an organic bridging group which contains from 1 to 6 bridging atoms, of which at least two are carbon atoms, and these can be unsubstituted or substituted.

Preferred groups X are —$CH_2$—, —$CH_2$—$CH_2$—, —$CH_2$—$CH_2$—$CH_2$—, —$CH_2$—$CH(CH_3)$—$CH_2$—, —$CH_2$—$C(CH_3)_2$—, —$CH_2$—, —$CH_2$—$C(C_2H_5)$, —$CH_2$—, —$CH_2$—$Si(CH_3)_2$—$CH_2$—, —$CH_2$—O—$CH_2$—, —$CH_2$—$CH_2$—$CH_2$—$CH_2$—, —$CH_2$—CH($C_2H_5$)—$CH_2$—, —$CH_2$—CH(n-Pr)—CH, and —$CH_2$—CH(n-Bu)—$CH_2$—, unsubstituted or substituted 1,2-phenyl moieties, unsubstituted or substituted 1,2-cyclohexyl moieties, unsubstituted or substituted 1,1'- or 1,2-ferrocenyl moieties, and/or unsubstituted or substituted 2,2'-(1,1'-biphenyl) moieties, unsubstituted or substituted 4,5-xanthene moieties, and/or unsubstituted or substituted oxydi-2,1-phenylene moieties.

Examples of suitable bidentate phosphine ligands are 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(di-tert-butylphosphino)ethane, 1,2-bis(dicyclohexylphosphino)ethane, 1,2-bis(diphenylphosphino)ethane, 1,3-bis(dicyclohexylphosphino)propane, 1,3-bis(diisopropylphosphino)propane, 1,3-bis(di-tert-butylphosphino)propane, 1,3-bis(diphenylphosphino)propane, 1,4-bis-(diisopropylphosphino)butane, 1,4-bis(diphenylphosphino)butane, 1,5-bis(dicyclohexylphosphino)pentane, 1,2-bis(di-tert-butylphosphino)benzene, 1,2-bis(diphenylphosphino)benzene, 1,2-bis(dicyclohexylphosphino)benzene, 1,2-bis(dicyclopentylphosphino)benzene, 1,3-bis(di-tert-butylphosphino)benzene, 1,3-bis(diphenylphosphino)benzene, 1,3-bis(dicyclohexylphosphino)benzene, 1,3-bis(dicyclopentylphosphino)benzene, 9,9-dimethyl-4,5-bis(diphenylphosphino)xanthene, 9,9-dimethyl-4,5-bis(diphenylphosphino)-2,7-di-tert-butylxanthene, 9,9-dimethyl-4,5-bis(di-tert-butylphosphino)xanthene, 1,1'-bis(diphenylphosphino)ferrocene, 2,2'-bis(diphenylphosphino)-1,1'-binaphthyl, 2,2'-bis(di-p-tolylphosphino)-1,1'-binaphthyl, (oxydi-2,1-phenylene)bis(diphenylphosphine), 2,5-(diisopropylphospholano)benzene, 2,3-O-isopropylidene-2,3-dihydroxy-1,4-bis(diphenylphosphino)butane, 2,2'-bis(di-tert-butylphosphino)-1,1'-biphenyl, 2,2'-bis(dicyclohexylphosphino)-1,1'-biphenyl, 2,2'-bis(diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenylphosphino)-2'-(N,N-dimethylamino)biphenyl, 2-(diphenylphosphino)ethylamine, 2-[2-(diphenylphosphino)ethyl]pyridine, 1,2-bis(di-4-sulfonatophenylphosphino)benzene tetrasodium salt, 1,2-bis(di-4-sulfonatophenylphosphino)benzene tetrapotassium salt, 1,2-bis(di-4-sulfonatophenylphosphino)benzene tetraammonium salt, (2,2'-bis[[bis(3-sulfonatophenyl)phosphino]methyl]-4,4',7,7'-tetrasulfonato-1,1'-binaphthyl octasodium salt, (2,2'-bis[[bis(3-sulfonatophenyl)phosphino]methyl]-4,4',7,7'-tetrasulfonato-1,1'-binaphthyl octapotassium salt, (2,2'-bis[[bis(3-sulfonatophenyl)phosphino]methyl]-4,4',7,7'-tetrasulfonato-1,1'-binaphthyl octaammonium salt, (2,2'-bis[[bis(3-sulfonatophenyl)phosphino]methyl]-5,5'-tetrasulfonato-1,1'-biphenyl hexasodium salt, (2,2'-bis[[bis(3-sulfonatophenyl)phosphino]methyl]-5,5'-tetrasulfonato-1,1'-biphenyl hexapotassium salt, (2,2'-bis[[bis(3-sulfonatophenyl)phosphino]methyl]-5,5'-tetrasulfonato-1,1'-biphenyl hexaammonium salt, (2,2'-bis[[bis(3-sulfonatophenyl)phosphino]methyl]-1,1'-binaphthyl tetrasodium salt, (2,2'-bis[[bis(3-sulfonatophenyl)phosphino]methyl]-1,1'-binaphthyl tetrapotassium salt, (2,2'-bis[[bis(3-sulfonatophenyl)phosphino]methyl]-1,1'-binaphthyl tetraammonium salt, (2,2'-bis[[bis(3-sulfonatophenyl)phosphino]methyl]-1,1'-biphenyl tetrasodium salt, (2,2'-bis[[bis(3-sulfonatophenyl)phosphino]methyl]-1,1'-biphenyl tetrapotassium salt, (2,2'-bis[[bis(3-sulfonatophenyl)phosphino]methyl]-1,1'-biphenyl tetraammonium salt, 9,9-dimethyl-4,5-bis(diphenylphosphino)-2,7-sulfonatoxanthene disodium salt, 9,9-dimethyl-4,5-bis(diphenylphosphino)-2,7-sulfonatoxanthene dipotassium salt, 9,9-dimethyl-4,5-bis(diphenylphosphino)-2,7-sulfonatoxanthene diammonium salt, 9,9-dimethyl-4,5-bis(di-tert-butylphosphino)-2,7-sulfonatoxanthene disodium salt, 9,9-dimethyl-4,5-bis(di-tert-butylphosphino)-2,7-sulfonatoxanthene dipotassium salt, 9,9-dimethyl-4,5-bis(di-tert-butylphosphino)-2,7-sulfonatoxanthene diammonium salt, 1,2-bis(di-4-sulfonatophenylphosphino)benzene tetrasodium salt, 1,2-bis(di-4-sulfonatophenylphosphino)benzene tetrapotassium salt, 1,2-bis(di-4-sulfonatophenylphosphino)benzene tetraammonium salt, meso-tetrakis(4-sulfonatophenyl)porphine tetrasodium salt, meso-tetrakis(4-sulfonatophenyl)porphine tetrapotassium salt, meso-tetrakis(4-sulfonatophenyl)porphine tetraammonium salt, meso-tetrakis(2,6-dichloro-3-sulfonatophenyl)porphine tetrasodium salt, meso-tetrakis(2,6-dichloro-3-sulfonatophenyl)porphine tetrapotassium salt, meso-tetrakis(2,6-dichloro-3-sulfonatophenyl)porphine tetraammonium salt, meso-tetrakis(3-sulfonatomesityl)porphine tetrasodium salt, meso-tetrakis(3-sulfonatomesityl)porphine tetrapotassium salt, meso-tetrakis(3-sulfonatomesityl)porphine tetraammonium salt, tetrakis(4-carboxyphenyl)porphine, 5,11,17,23-sulfonato-25,26,27,28-tetrahydroxycalix[4]arene.

The moieties $R^5$ and/or the bridging group can moreover bond the ligands of the formula III or IV to a suitable polymer or inorganic substrate.

It is preferable that the molar transition metal-ligand ratio of the catalyst system is from 1:0.01 to 1:100.

It is particularly preferable that the molar transition metal-ligand ratio of the catalyst system is from 1:0.05 to 1:10.

It is very particularly preferable that the molar transition metal-ligand ratio of the catalyst system is from 1:1 to 1:4.

It is preferable that the catalyst system is generated prior to the reaction and/or at the start of the reaction and/or during the reaction in situ.

It is preferable that the catalyst acts as homogeneous and/or heterogeneous catalyst during the reaction.

It is preferable, during the reaction, that the heterogeneous catalyst takes the form of a suspension or a form bonded to a solid phase.

It is preferable that the reaction takes place in a solvent in the form of a single-phase system, in a homogeneous or heterogeneous mixture, and/or in the gas phase. The reaction in a solvent is advantageous because less heat is produced and consequently there is less formation of by-products.

If a multiphase system is used it is also possible to use a phase-transfer catalyst.

Suitable solvents are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloroethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc. One or more of these compounds can be used, alone or in combination.

Suitable solvents also encompass the phosphinic acid sources and olefins used. These have advantages in the form of higher space-time yield.

It is preferable that the reaction is carried out under the autogenous vapor pressure of the olefin and/or of the solvent.

In particular, the reaction takes place in an atmosphere which comprises further gaseous constituents, e.g. nitrogen, oxygen, or argon.

It is preferable that the partial pressure of the olefin during the reaction is from 0.01 to 100 bar.

It is particularly preferable that the partial pressure of the olefin during the reaction is from 0.1 to 10 bar.

It is preferable that the reaction is carried out at a temperature of from −20 to 340° C.

It is particularly preferable that the reaction is carried out at a temperature of from 20 to 180° C.

It is preferable that the total pressure during the reaction is from 1 to 100 bar.

It is preferable that the molar phosphinic acid-olefin ratio used for the reaction is from 1:10 000 to 1:0.001.

It is particularly preferable that the molar phosphinic acid-olefin ratio used for the reaction is from 1:30 to 1:0.01.

It is preferable that the molar phosphinic acid-catalyst ratio used for the reaction is from 1:1 to 1:0.00000001.

It is particularly preferable that the molar phosphinic acid-catalyst ratio used for the reaction is from 1:0.01 to 1:0.000001.

It is preferable that the molar phosphinic acid-solvent ratio used for the reaction is from 1:10 000 to 1:0.

It is particularly preferable that the molar phosphinic acid-solvent ratio used for the reaction is from 1:50 to 1:1.

A characteristic of a process of the invention for the production of alkylphosphonous acids, of alkylphosphonous salts, and of alkylphosphonous esters is that a source of phosphinic acid is reacted with olefins in the presence of a catalyst, and the product (alkylphosphonous acid, alkylphosphonous salts, alkylphosphonous esters) is freed from catalyst, transition metal or transition metal compound, ligand, complexing agent, salts, and by-products.

The invention removes the solvent by distillation and/or extraction.

The invention removes the catalyst, the catalyst system, the transition metal, and/or the transition metal compound via addition of an auxiliary 1 and removal of the catalyst, of the catalyst system, of the transition metal, and/or of the transition metal compound via extraction and/or filtration.

The invention removes the catalyst, the catalyst system, the transition metal, and/or the transition metal compound via extraction and/or filtration.

The invention removes the ligand and/or complexing agent via extraction using auxiliary 2 of the invention, and/or distillation using auxiliary 2 of the invention.

The invention removes the auxiliaries via distillation and/or filtration and/or extraction.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr, metal carbonates, such as barium carbonate, calcium carbonate, strontium carbonate, metal sulfates, such as barium sulfate, calcium sulfate, strontium sulfate, metal phosphates, such as aluminum phosphate, vanadium phosphate, metal carbides, such as silicon carbide, metal aluminates, such as calcium aluminate, metal silicates, such as aluminum silicate, chalks, zeolites, bentonite, montmorillonite, hectorite, functionalized silicates, functionalized silica gels, such as SiliaBond®, QuadraSil™, functionalized polysiloxanes, such as Deloxan®, metal nitrides, carbon, activated charcoal, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®, functionalized polymers, such as Chelex®, QuadraPure™, Smopex®, PolyOrgs®, polymer-bound phosphanes, phosphane oxides, phosphinates, phosphonates, phosphates, amines, ammonium salts, amides, thioamides, urea, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

It is preferable that the amounts added of auxiliary 1 correspond to from 0.1 to 40% by weight loading of the metal, based on auxiliary 1.

It is preferable that auxiliary 1 is used at temperatures of from 20 to 90° C.

It is preferable that the residence time of auxiliary 1 is from 0.5 to 360 minutes.

It is preferable that auxiliary 2 is the abovementioned solvent of the invention.

It is preferable that the work-up of the reaction mixture differs as a function of the type of reaction selected, using a single- or multiphase system with homogeneous and/or heterogeneous catalyst, and the solubilities of the products and starting materials in the solvent system selected.

Single-Phase System

A heterogeneous catalyst can act within the suspension or after binding to a stationary phase.

If the heterogeneous catalyst takes the form of a suspension, it is filtered from the reaction mixture and can be made available for further reactions. The phase comprising the product (alkylphosphonous acid), and/or comprising the source of phosphinic acid, and/or comprising the olefin is passed onward for product isolation.

If the heterogeneous catalyst has been bound to a stationary phase, and if the product is soluble in the phase, the phase comprising the product, and/or comprising the source of phosphinic acid, and/or comprising the olefin is passed onward for product isolation.

If the heterogeneous catalyst has been bonded to a stationary phase and if the product is insoluble in the phase, the product is filtered from the solvent system. The circulation system can be used for the phase comprising the source of phosphinic acid and comprising the olefin.

If a homogeneous catalyst is used and the product is soluble in the solvent system, the catalyst and/or the element in its zero-valency or positively charged, ionic form is separated from the reaction mixture by crystallization, adsorption, absorption, precipitation, ion exchange, distillation, or extraction, once the reaction has ended. The phase comprising the product, and/or comprising the source of phosphinic acid, and/or comprising the olefin is passed onward for product isolation.

If a homogeneous catalyst is used and the product is insoluble in the solvent system, the product is filtered from the solvent system. The circulation system can be used for the phase comprising the catalyst, comprising the source of phosphinic acid, and comprising the olefin.

Multiphase System

A feature of a multiphase system is a suitable choice of a solvent system, a characteristic being that product and catalyst are present in different phases, or the product does not dissolve in any of the phases.

If the product is not dissolved in any of the phases, it is filtered from the solvent system. A circulation system can be used for the phase(s) comprising the catalyst system, comprising the source of phosphinic acid, and comprising the olefin.

If the product is soluble in one of the phases, the circulation system can be used for the phase(s) comprising the catalyst system, and/or comprising the source of phosphinic acid, and/or comprising olefin. The phase(s) comprising the product, and/or comprising the source of phosphinic acid, and/or comprising the olefin is/are passed onward for product isolation.

The isolation of the product and/or of the olefin and/or of the transition metal and/or of the transition metal compound and/or catalyst system and/or of the ligand and/or of the source of phosphinic acid proceeds from a solution in the solvent system previously used, via removal of the solvent system by means of distillation or rectification, via crystallization of the product and/or olefin and/or of the source of phosphinic acid in a suitable solvent system, via precipitation of the product and/or olefin and/or of the source of phosphinic acid in a suitable solvent system, via filtration or centrifuging, distillation, rectification, extraction, adsorption, or chromatography of the product and/or olefin and/or of the source of phosphinic acid.

A feature of the work-up and isolation of the product is that it is composed of at least one of the abovementioned methods and/or a combination of these.

In one embodiment of the process, the individual components (olefin, catalyst, source of phosphinic acid, optionally solvent, gaseous constituents) can be used simultaneously or in any conceivable sequence; the sequence selected here affects the yield of alkylphosphonous acid.

It is preferable that the reaction is conducted by
a) using the catalyst as initial charge in a solvent, and adding the source of phosphinic acid and then the olefin,
b) using the catalyst as initial charge in a solvent, and adding the olefin and then the source of phosphinic acid,
c) using the catalyst as initial charge and adding the source of phosphinic acid and then the olefin,
d) using the catalyst as initial charge and adding the olefin and then the source of phosphinic acid,
e) using the source of phosphinic acid as initial charge in a solvent and adding catalyst and then olefin,
f) using the source of phosphinic acid as initial charge in a solvent and adding olefin and then catalyst,
g) using the source of phosphinic acid as initial charge and adding catalyst and then olefin,
h) using the source of phosphinic acid as initial charge and adding olefin and then catalyst,
i) using the olefin as initial charge in a solvent and adding the source of phosphinic acid and then the catalyst,
j) using the olefin as initial charge in a solvent and adding the catalyst and then the source of phosphinic acid,
k) using the olefin as initial charge and adding the source of phosphinic acid and then the catalyst,
l) using the olefin as initial charge and adding the catalyst and then the source of phosphinic acid.

When the processes a) to l) are compared with other conceivable combinations they provide advantages in the form of higher yields and smaller amount of oxidation products.

In one embodiment of the process, olefin, ligand, and source of phosphinic acid are used as initial charge in a solvent, and the transition metal or the transition metal compound is added.

In one embodiment of the process, olefin, ligand, and source of phosphinic acid are used as initial charge, and the transition metal or the transition metal compound is added.

In one embodiment of the process, the homogeneous and/or heterogeneous catalyst can be generated prior to the reaction and/or at the start of the reaction in situ and/or during the reaction in situ.

In one embodiment of the process, the reaction can proceed in a single-phase system, in a homogeneous or heterogeneous mixture, and/or in the gas phase.

In one embodiment of the process, a multiphase system can be used and a phase-transfer catalyst can also be used. In this case, the circulation system can be used for the phase(s) comprising the catalyst system, and the phase(s) comprising the product can be passed onward for work-up.

One embodiment of the process produces enantiomerically pure or enantiomerically enriched alkylphosphonous acids and their derivatives. This requires chiral bidentate ligands of the general formula (IV). Examples of ligands preferred in the invention are (2S,2S)-(−)-bis(diphenylphosphino)butane, (2R,2R)-(+)-bis(diphenylphosphino)butane, (+)-1,2-bis[(2R,5R)-2,5-diidopropylphospholano]benzene, (−)-1,2-bis[(2S,5S)-2,5-diidopropylphospholano]benzene, (+)-2,3-O-isopropropylidene-2,3-dihydroxy-1,4-bis(diphenylphosphino)butane, (+2,3-O-isopropropylidene-2,3-dihydroxy-1,4-bis(diphenylphosphino)butane, (R)-(+)-2,2'-bis(diphenylphosphino)-1,1'-binaphthyl, (S)-(−)-2,2'-bis(diphenylphosphino)-1,1'-binaphthyln, (R)-(+)-2,2'-bis(di-p-tolylphosphino)-1,1'-binaphthyl, (S)-(+2,2'-bis(di-p-tolylphosphino)-1,1'-binaphthyl, (R)-(+)-7,7'-bis[di(3,5-dimethylphenyl)phosphino]-2,2',3,3'-tetrahydro-1,1'-spirobiindane, (S)-(−)-7,7'-bis[di(3,5-dimethylphenyl)phosphino]-2,2',3,3'-tetrahydro-1,1'-spirobiindane, 1,1'-bis((2R,5R)-2,5-diethylphospholano)ferrocene, 1,1'-bis((2S,5S)-2,5-diethylphospholano)ferrocene.

One preferred embodiment of the process reacts phosphinic acid and/or its sodium salt with ethylene in the presence of a catalyst in a solvent to give ethylphosphonous acid and/or the sodium salt as main product.

It is preferable that the reaction proceeds in absorption columns, spray towers, bubble columns, stirred tanks, flow tubes, and/or kneaders.

In the case of heterogeneous catalysts, it is preferable to use flow tubes.

It is preferable that the mixing units used comprise anchor stirrers, blade stirrers, MIG stirrers, propeller stirrers, impeller stirrers, turbine stirrers, cross beaters, disperser disks, cavitation (gasification) stirrers, rotor-stator mixers, static mixers, Venturi nozzles, and/or mammoth pumps.

It is preferable that the intensity of mixing of the reaction solution during the reaction corresponds to a rotation Reynolds number of from 1 to 1 000 000, preferably from 100 to 100 000.

It is preferable that olefin, catalyst, solvent system, and hypophosphorous acid and/or salts thereof are intimately mixed with introduction of the following amount of energy: from 0.080 to 10 kW/m$^3$, preferably from 0.30 to 1.65 kW/m$^3$.

It is preferable that the acid number of the alkylphosphonous acids, alkylphosphonous salts, and alkylphosphonous esters of the invention, and/or alkylphosphonous acids, alkylphosphonous salts, and alkylphosphonous esters produced by a process of the invention is >0.32 g KOH/g of alkylphosphonous acid. The high acid number here is advantageous for a high degree of crosslinking of thermoset polymers.

It is preferable that the alkylphosphonous acids, alkylphosphonous salts, and alkylphosphonous esters of the invention, and/or alkylphosphonous acids, alkylphosphonous salts, and alkylphosphonous esters produced by a process of the invention are used
- as binders, e.g. for foundry materials and molding sands,
- as crosslinking agents or, respectively, accelerator in the hardening of epoxy resins, of polyurethanes, or of unsaturated polyester resins,
- as polymer stabilizers, e.g. as light stabilizer and/or heat stabilizers for cotton textiles, polymer fibers, or plastics,
- as plant-protection agents, e.g. as plant-growth regulator, or as herbicide, pesticide, or fungicide,
- as therapeutic agent or additive in therapeutic agents for humans or animals, e.g. as enzyme modulator, or for stimulation of tissue growth,
- as sequestering agents, e.g. for the control of deposits in industrial water supply systems, or in petroleum production or in metal-treatment agents,
- as petroleum additive, e.g. as antioxidant and for increasing octane number,
- as corrosion-protection agents,
- in laundry-detergent and cleaning-product applications, e.g. as decolorizer,
- in electronics applications, e.g. in polyelectrolytes for capacitors, batteries, and accumulators, and also as free-radical scavengers in photosensitive layers, or
- as precursor for the production of alkylphosphonic acids.

It is preferable that the alkylphosphonous acids, alkylphosphonous salts, and alkylphosphonous esters of the invention, and/or alkylphosphonous acids, alkylphosphonous salts, and alkylphosphonous esters produced by a process of the invention are used for the production of flame-retardant thermoplastic polymer molding compositions.

It is preferable that the flame-retardant thermoplastic polymer molding composition comprises from 0.5 to 45% by weight of alkylphosphonous acid, alkylphosphonous salt, or alkylphosphonous ester of the invention, and/or alkylphosphonous acid, alkylphosphonous salt, or alkylphosphonous ester produced by a process of the invention, It is preferable that the flame-retardant thermoplastic polymer molding composition comprises from 0.5 to 45% by weight of alkylphosphonous acid, alkylphosphonous salt, or alkylphosphonous ester of the invention, or of alkylphosphonous acid, alkylphosphonous salt, or alkylphosphonous ester produced by a process of the invention, and from 0.5 to 95% by weight of thermoplastic polymer or a mixture of the same, where the entirety of the components is 100% by weight.

It is preferable that the flame-retardant thermoplastic polymer molding composition comprises from 10 to 40% by weight of alkylphosphonous acid, alkylphosphonous salt, or alkylphosphonous ester of the invention, and/or alkylphosphonous acid, alkylphosphonous salt, or alkylphosphonous ester produced by a process of the invention, from 10 to 80% by weight of thermoplastic polymer or a mixture of the same, from 2 to 40% by weight of additives, and from 2 to 40% by weight of filler or reinforcing materials, where the entirety of the components is 100% by weight.

A characteristic of the process for the production of flame-retardant thermoplastic polymer molding compositions is that the alkylphosphonous acid, alkylphosphonous salt, or alkylphosphonous ester of the invention, and/or alkylphosphonous acid, alkylphosphonous salt, or alkylphosphonous ester produced by a process of the invention is mixed with the polymer pellets and any additives and the materials are incorporated in a twin-screw extruder (ZSK 25 WLE, 14.5 kg/h, 200 rpm, L/D: 4) at temperatures of 170° C. (polystyrene), about 270° C. (PET, polyethylene terephthalate), from 230 to 260° C. (polybutylene terephthalate, PBT), or of 260° C. (PA6) or from 260 to 280° C. (PA 66). The homogenized polymer extrudate is drawn off, cooled in a water bath, and then pelletized, and dried until its residual moisture content is from 0.05 to 5%, preferably from 0.1 to 1% by weight.

A characteristic of the process for the production of a flame-retardant thermoplastic polymer molding composition is that 1000 parts by weight of dimethyl terephthalate and 720 parts by weight of ethylene glycol, and from 35 to 700 parts by weight of alkylphosphonous acid, alkylphosphonous salt, or alkylphosphonous ester of the invention, and/or alkylphosphonous acid, alkylphosphonous salt, or alkylphosphonous ester produced by a process of the invention are polymerized. The polymerization process can optionally proceed in the presence of zinc acetate. The flame-retardant polymer molding composition can optionally be spun to give fibers.

It is preferable that the polymer is a thermoplastic or thermoset polymer.

It is preferable that the thermoplastic polymers are polymers of mono- and diolefins, for example polypropylene, polyisobutylene, poly-1-butene, poly-4-methyl-1-pentene, polyisoprene, and polybutadiene, or else polymers of cycloolefins, e.g. of cyclopentene or norbornene; or polyethylene (which may, where appropriate, have been crosslinked), e.g. high-density polyethylene (HDPE), high-density high-molecular-weight polyethylene (HMWHDPE), high-density ultrahigh-molecular-weight polyethylene (UHMWHDPE), medium-density polyethylene (HDPE), low-density polyethylene (LDPE), linear low-density polyethylene (LLDPE), or branched low-density polyethylene (VLDPE), or a mixture thereof.

It is preferable that the thermoplastic polymers are copolymers of mono- and diolefins with one another or with other vinyl monomers, e.g. ethylene-propylene copolymers, linear low-density polyethylene (LLDPE), or a mixture of this with low-density polyethylene (LDPE), propylene-1-butene copolymers, propylene-isobutylene copolymers, ethylene-1-butene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide, or ethylene-acrylic acid copolymers and their salts (ionomers), or else terpolymers of ethylene with propylene and with a diene, such as hexadiene, dicyclopentadiene, or ethylidenenorbornene; or a mixture of these copolymers with one another, e.g. polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers, and alternating or random-structure polyalkylene/carbon monoxide copolymers, or a mixture of these with other polymers, e.g. with polyamides.

It is preferable that the polymers are hydrocarbon resins (e.g. $C_5$-$C_9$) inclusive of hydrogenated modifications thereof (e.g. tackifier resins), and mixtures of polyalkylenes and starch.

It is preferable that the thermoplastic polymers are polystyrene, polyp-methylstyrene), and/or poly(alpha-methylstyrene).

It is preferable that the thermoplastic polymers are copolymers of styrene or alpha-methylstyrene with dienes or with acrylic derivatives, e.g. styrene-butadiene, styrene-acrylonitrile, styrene-alkyl methacrylate, styrene-butadiene-alkyl acrylate and the corresponding methacrylate, styrene-maleic anhydride, styrene-acrylonitrile-methyl acrylate; a mixture of high impact resistance composed of styrene copolymers and of another polymer, e.g. of a polyacrylate, of a diene polymer, or of an ethylene-propylene-diene terpolymer; or else block copolymers of styrene, e.g. styrene-butadiene-styrene, styrene-isoprene-styrene, styrene-ethylene/butylene-styrene, or styrene-ethylene/propylene-styrene.

It is preferable that the thermoplastic polymers are graft copolymers of styrene or alpha-methylstyrene, e.g. styrene on polybutadiene, styrene on polybutadiene-styrene copolymers or on polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates and, respectively, alkyl methacrylates on polybutadiene, styrene and acrylonitrile on ethylene-propylene-diene terpolymers, styrene and acrylonitrile on polyalkyl acrylates or on polyalkyl methacrylates, styrene and acrylonitrile on acrylate-butadiene copolymers, or else a mixture of these, for example that known as ABS polymer, MBS polymer, ASA polymer, or AES polymer.

It is preferable that the thermoplastic polymers are halogen-containing polymers, e.g. polychloroprene, chlorinated rubber, chlorinated and brominated copolymer composed of isobutylene-isoprene (halobutyl rubber), chlorinated or chlorosulfonated polyethylene, copolymers of ethylene and of chlorinated ethylene, epichlorohydrin homo- and copolymers, in particular polymers composed of halogen-containing vinyl compounds, e.g. polyvinyl chloride, polyvinylidene chloride, polyvinyl fluoride, polyvinylidene fluoride; or else copolymers of these, such as vinyl chloride-vinylidene chloride, vinyl chloride-vinyl acetate, or vinylidene chloride-vinyl acetate.

It is preferable that the thermoplastic polymers are polymers which derive from alpha,beta-unsaturated acids and from their derivatives, e.g. polyacrylates and polymethacrylates, butyl-acrylate-impact-modified polymethyl methacrylates, polyacrylamides and polyacrylonitriles, and copolymers of the monomers mentioned with one another or with other unsaturated monomers, e.g. acrylonitrile-butadiene copolymers, acrylonitrile-alkyl acrylate copolymers, acrylonitrile-alkoxyalkyl acrylate copolymers, acrylonitrile-vinyl halide copolymers, or acrylonitrile-alkyl methacrylate-butadiene terpolymers.

It is preferable that the thermoplastic polymers are polymers which derive from unsaturated alcohols and amines or from their acyl derivatives or acetals, e.g. polyvinyl alcohol, polyvinyl acetate, polyvinyl stearate, polyvinyl benzoate, polyvinyl maleate, polyvinyl butyral, polyallyl phthalate, polyallylmelamine; or else their copolymers with olefins.

It is preferable that the thermoplastic polymers are homo- and copolymers of cyclic ethers, e.g. polyalkylene glycols, polyethylene oxide, polypropylene oxide, or their copolymers with bisglycidyl ethers.

It is preferable that the polymers are thermoplastic polyacetals, such as polyoxymethylene, or else those polyoxymethylenes which contain comonomers, e.g. ethylene oxide; polyacetals modified with thermoplastic polyurethanes, or with acrylates, or with MBS.

It is preferable that the thermoplastic polymers are polyphenylene oxides and polyphenylene sulfides, and their mixtures with styrene polymers or with polyamides.

It is preferable that the thermoplastic polymers are polyurethanes which derive firstly from polyethers, polyesters, and polybutadienes having terminal hydroxy groups, and secondly from aliphatic or aromatic polyisocyanates, or else are precursors of these.

It is preferable that the thermoplastic polymers are polyamides and copolyamides derived from diamines and dicarboxylic acids, and/or from aminocarboxylic acids, or from the corresponding lactams, for example nylon-4, nylon-6 (Akulon® K122, DSM; Zytel® 7301, DuPont; Durethan® B 29, Bayer), nylon-6,6 (Zytel® 101, DuPont; Durethan® A30, Durethan® AKV, Durethan® AM, Bayer; Ultramid® A3, BASF)-6,10, -6,9, -6,12, -4,6, -12,12, nylon-11, and nylon-12 (Grillamid® L20, Ems Chemie), aromatic polyamides based on m-xylene, diamine and adipic acid; polyamides prepared from hexamethylenediamine and iso- and/or terephthalic acid and, where appropriate, an elastomer as modifier, e.g. poly-2,4,4-trimethylhexamethyleneterephthalamide or poly-m-phenyleneisophthalamide. Other suitable polymers are block copolymers of the abovementioned polyamides with polyolefins, with olefin copolymers, with ionomers, or with chemically bonded or grafted elastomers; or with polyethers, e.g. with polyethylene glycol, polypropylene glycol, or polytetramethylene glycol. EPDM- or ABS-modified polyamides or copolyamides are also suitable, as are polyamides condensed during processing ("RIM polyamide systems").

It is preferable that the polymers are polyureas, polyimides, polyamideimides, polyetherimides, polyesterimides, polyhydantoins and polybenzimidazoles.

It is preferable that the thermoplastic polymers are polyesters which derive from dicarboxylic acids and dialcohols and/or from hydroxycarboxylic acids, or from the corresponding lactones, for example polyethylene terephthalate, polybutylene terephthalate (Cefanex® 2500, Celanex® 2002, Celanese; Ultradur®, BASF), poly-1,4-dimethylolcyclohexane terephthalate, polyhydroxybenzoates, and also block polyetheresters which derive from polyethers having hydroxyl end groups; as well as polyesters modified with polycarbonates or with MBS.

It is preferable that the thermoplastic polymers are polycarbonates or polyester carbonates, or else polysulfones, polyether sulfones, or polyether ketones.

It is preferable that the polymers are mixtures (polyblends) of the above-mentioned polymers, e.g. PP/EPDM, nylon/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PU, PC/thermoplastic PU, POM/acrylate, POM/MBS, PPO/HIPS, PPO/nylon-6,6 and copolymers, PA/HDPE, PA/PP, PA/PPO, PBT/PC/ABS, and PBT/PET/PC.

It is preferable that the alkylphosphonous acid, alkylphosphonous salt, and alkylphosphonous ester of the invention, and/or alkylphosphonous acid, alkylphosphonous salt, and alkylphosphonous ester produced by a process of the invention, is used for the production of flame-retardant polymer moldings, polymer films, polymer filaments, and polymer fibers.

It is preferable that the flame-retardant polymer moldings, polymer films, polymer filaments, and polymer fibers comprise from 0.5 to 45% by weight of alkylphosphonous acid, alkylphosphonous salt, or alkylphosphonous ester of the invention, and/or alkylphosphonous acid, alkylphosphonous salt, and alkylphosphonous ester produced by a process of the invention, and from 0.5 to 99.5% by weight of thermoplastic polymer, or a mixture of the same.

It is preferable that the flame-retardant polymer moldings, polymer films, polymer filaments, and polymer fibers comprise from 0.5 to 45% by weight of alkylphosphonous acid, alkylphosphonous salt, or alkylphosphonous ester of the invention, and/or alkylphosphonous acid, alkylphosphonous salt, and alkylphosphonous ester produced by a process of the invention, and from 0.5 to 98.5% by weight of thermoplastic polymer, or a mixture of the same, from 0.5 to 55% by weight of additives, and from 0.5 to 55% by weight of filler or reinforcing materials.

Finally, the invention also provides a process for the production of flame-retardant polymer moldings, which comprises processing inventive flame-retardant polymer molding compositions via injection molding (e.g. an injection-molding machine (Aarburg Allrounder) and compression molding, foam injection molding, internal-gas-pressure injection molding, blow molding, cast-film production, calendering, lamination, or coating at relatively high temperatures to give the flame-retardant polymer molding.

A characteristic of the process for the production of flame-retardant polymer moldings is that the flame-retardant molding composition of the invention is processed at suitable melt temperatures to give polymer moldings.

Suitable preferred melt temperatures are from 200 to 250° C. for polystyrene, from 200 to 300° C. for polypropylene, from 250 to 290° C. for polyethylene terephthalate (PET), from 230 to 270° C. for polybutylene terephthalate (PBT), from 260 to 290° C. for nylon-6 (PA 6), from 260 to 290° C. for nylon-6,6 (PA 6.6), and from 280 to 320° C. for polycarbonate.

It is preferable that the thermoset polymers are unsaturated polyester resins which derive from copolyesters of saturated and unsaturated dicarboxylic acids or their anhydrides with polyhydric alcohols, or else vinyl compounds, as crosslinking agents. UP resins are hardened via free-radical polymerization using initiators (e.g. peroxides) and accelerators.

Preferred unsaturated dicarboxylic acids and unsaturated dicarboxylic acid derivatives for the preparation of the polyesters are maleic anhydride and fumaric acid.

Preferred saturated dicarboxylic acids are phthalic acid, isophthalic acid, terephthalic acid, tetrahydrophthalic acid, and adipic acid.

Preferred diols are 1,2-propanediol, ethylene glycol, diethylene glycol, and neopentyl glycol, neopentyl glycol, and ethoxylated or propoxylated bisphenol A.

Preferred vinyl compound for the crosslinking reaction is styrene.

Preferred hardener systems are peroxides and metal coinitiators, e.g. hydroperoxides, and cobalt octanoate, and/or benzoyl peroxide, and aromatic amines, and/or UV light and photosensitizers, e.g. benzoin ethers.

Preferred hydroperoxides are di-tert-butyl peroxide, tert-butyl peroctoate, tert-butyl perpivalate, tert-butyl 2-ethylperhexanoate, tert-butyl pennaleate, tert-butyl periso-butyrate, benzoyl peroxide, diacetyl peroxide, succinyl peroxide, p-chlorobenzoyl peroxide, dicyclohexyl peroxydicarbonate.

It is preferable that the amounts used of initiators are from 0.1 to 20% by weight, with preference from 0.2 to 15% by weight, based on the weight of all the comonomers.

Preferred metal coinitiators are compounds of cobalt, of manganese, of iron, of vanadium, of nickel, or of lead. It is preferable to use amounts of from 0.05 to 1% by weight, based on the weight of all of the comonomers, of metal coinitiators.

Preferred aromatic amines are dimethylaniline, p-dimethyltoluene, diethylaniline and phenyldiethanolamines.

A characteristic of a process for the production of flame-retardant copolymers is that (A) at least one ethylenically unsaturated dicarboxylic anhydride derived from at least one $C_4$-$C_8$ dicarboxylic acid, (B) at least one vinylaromatic compound, and (C) one polyol are copolymerized, and (D) are reacted with alkylphosphonous acid, alkylphosphonous salt, or alkylphosphonous ester of the invention, and/or alkylphosphonous acid, alkylphosphonous salt, or alkylphosphonous ester produced by a process of the invention.

A characteristic of a process for the production of flame-retardant thermoset compositions is that a thermoset resin is mixed with a flame-retardant component made of alkylphosphonous acid, alkylphosphonous salt, or alkylphosphonous ester of the invention, and/or alkylphosphonous acid, alkylphosphonous salt, or alkylphosphonous ester produced by a process of the invention, and the resultant mixture is wet-pressed at pressures of from 3 to 10 bar and temperatures of from 20 to 60° C. (cold pressing).

A characteristic of a process for the production of flame-retardant thermoset compositions is that a thermoset resin is mixed with alkylphosphonous acid, alkylphosphonous salt, or alkylphosphonous ester of the invention, and/or alkylphosphonous acid, alkylphosphonous salt, or alkylphosphonous ester produced by a process of the invention, and the resultant mixture is wet-pressed at pressures of from 3 to 10 bar and temperatures of from 80 to 150° C. (warm or hot pressing).

It is preferable that the polymers are crosslinked epoxy resins which derive from aliphatic, cycloaliphatic, heterocyclic, or aromatic glycidyl compounds, e.g. products of bisphenol A diglycidyl ethers or of bisphenol F diglycidyl ethers, which are crosslinked by means of conventional hardeners and/or accelerators.

Suitable glycidyl compounds are bisphenol A diglycidyl ester, bisphenol F diglycidyl ester, polyglycidyl ester of phenol-formaldehyde resins and of cresol-formaldehyde resins, polyglycidyl ester of pthtalic, isophthalic, and terephthalic acid, and also of trimellitic acid, N-glycidyl compounds of aromatic amines and of heterocyclic nitrogen bases, and also di- and polyglycidyl compounds of polyhydric aliphatic alcohols.

Suitable hardeners are polyamines, such as diethylenetriamine, triethylenetetramine, aminoethylpiperazine, isophoronediamine, polyamidoamine, diaminodiphenylmethane, diaminodiphenol sulfones, and dicyandiamide.

Suitable hardeners are polybasic acids or their anhydrides, e.g. phthalic anhydride, maleic anhydride, tetrahydrophthalic anhydride, methyltetrahydrophthalic anhydride, hexahydrophthalic anhydride, and methylhexahydrophthalic anhydride.

Suitable hardeners are phenols, e.g. phenol-novolak resin, cresol-novolak resin, dicyclopentadiene-phenol-adduct resin, phenol-aralkyl resin, cresol-aralkyl resin, naphthol-aralkyl resin, biphenol-modified phenol-aralkyl resin, phenol-trimethylolmethane resin, tetraphenylolethane resin, naphthol-novolak resin, naphthol-phenol cocondensate resin, naphthol-cresol cocondensate resin, biphenol-modified phenolic resin, and aminotriazine-modified phenolic resin.

These hardeners can be used alone or in combination with one another.

Suitable catalysts or accelerators for the crosslinking reaction during the polymerization reaction are tertiary amines, benzyldimethylamine, N-alkylpyridines, imidazole, 1-methylimidazole, 2-methylimidazole, 2-ethyl-4-methylimidazole, 2-ethyl-4-methylimidazole, 2-phenylimidazole, 2-heptadecylimidazole, a metal salt of organic acids, Lewis acids, and amine complex salts.

Epoxy resins are suitable for the potting of electrical or electronic components, and for saturation and impregnation processes. In electrical engineering, the epoxy resins used are mainly flame-retardant, and used for printed circuit boards and insulators.

It is preferable that the polymers are crosslinked polymers which derive on the one hand from aldehydes and on the other hand from phenols, urea, or melamine, examples being phenol-formaldehyde resins, urea-formaldehyde resins, and melamine-formaldehyde resins.

It is preferable that the polymers are crosslinkable acrylic resins which derive from substituted acrylates, e.g. from epoxy acrylates, from urethane acrylates, or from polyester acrylates.

It is preferable that the polymers are alkyd resins, polyester resins, and acrylate resins, crosslinked with melamine resins, with urea resins, with isocyanates, with isocyanurates, with polyisocyanates, or with epoxy resins.

The invention also provides a flame-retardant polyurethane molding composition produced via reaction of from 0.1 to 50 parts by weight of alkylphosphonous acid, alkylphosphonous salt, or alkylphosphonous ester of the invention, and/or alkylphosphonous acid, alkylphosphonous salt, or alkylphosphonous ester produced by a process of the invention, with from 30 to 65 parts by weight of polyisocyanate and with from 30 to 65 parts by weight of polyol.

A characteristic of the process for the production of a flame-retardane polyurethane molding composition is that from 170 to 70 parts by weight, preferably from 130 to 80 parts by weight, of polyisocyanates are reacted with 100 parts by weight of polyol, with from 0.1 to 50 parts by weight of alkylphosphonous acid, alkylphosphonous salt, or alkylphosphonous ester of the invention, and/or alkylphosphonous acid, alkylphosphonous salt or alkylphosphonous ester produced by a process of the invention, and with from 0.1 to 4 parts by weight, particularly preferably from 1 to 2 parts by weight, of catalyst, and foamed optionally with from 0.1 to 1.8 parts by weight, preferably from 0.3 to 1.6 parts by weight, of blowing agent.

Preferred polyols are alkene oxide adducts of ethylene glycol, 1,2-propanediol, bisphenol A, trimethylolpropane, glycerol, pentaerythrol, sorbitol, sugars, degraded starch, ethylenediamine, diaminotoluene, and/or aniline, these serving as an initiator. The preferred alkoxylating agents preferably contain from 2 to 4 carbon atoms, particular preference being given to ethylene oxide and propylene oxide.

Preferred polyester polyols are obtained via polycondensation of a polyalcohol, such as ethylene glycol, diethylene glycol, propylene glycol, 1,4-butanediol, 1,5-pentanediol, methylpentanediol, 1,6-hexanediol, trimethylolpropane, glycerol, pentaerythritol, diglycerol, glucose and/or sorbitol, with a dibasic acid, such as oxalic acid, malonic acid, succinic acid, tartaric acid, adipic acid, sebacic acid, maleic acid, fumaric acid, phthalic acid, terephthalic acid. These polyester polyols can be used alone or in combination.

Suitable polyisocyanates are aromatic, alicyclic, or aliphatic polyisocyanates having no fewer than two isocyanate groups, and mixtures thereof. Preference is given to aromatic polyisocyanates, such as tolyl diisocyanate, methylenediphenyl diisocyanate, naphthylene diisocyanates, xylylene diisocyanate, tris(4-isocyanatophenyl)methane, and polymethylenepolyphenylene diisocyanates; alicyclic polyisocyanates are methylenediphenyl diisocyanate, and tolyl diisocyanate; and aliphatic polyisocyanates are hexamethylene diisocyanate, isophorene diisocyanate, demeryl diisocyanate, 1,1-methylenebis(4-isocyanatocyclohexane-4,4'-diisocyanatodicyclohexylmethane isomer mixture, cyclohexyl 1,4-diisocyanate, Desmodur® grades (Bayer) and lysine diisocyanate, and mixtures thereof.

Suitable polyisocyanates are modified products obtained via reaction of polyisocyanate with polyol, urea, carbodiimide, and/or biuret.

Suitable catalysts are strong bases, alkali metal salts of carboxylic acids, or aliphatic tertiary amines. Preference is given to quaternary ammonium hydroxide, alkali metal hydroxide or alkoxide, sodium or potassium acetate, potassium octoate, sodium benzoate, 1,4-diazabicyclo[2.2.2]octane, N,N,N,N-tetramethylhexamethylenediamine, N,N,N', N'-tetramethylpropylenediamine, N,N,N',N,N''-pentamethyldiethylenetriamine, trimethylaminoethylpiperazine, N,N-dimethylcyclohexylamine, N,N-dimethylbenzylamine, N-methylmorpholine, N-ethylmorpholine, trimethylamine, triethylamine, tributylamine, triethylenediamine, bis(dimethylaminoalkyl)piperazine, N,N,N',N'-tetramethylethylenediamine, N,N-diethylbenzylamine, bis(N,N-diethylaminoethyl)adipate, N,N,N', N'-tetramethyl-1,3-butanediamine, N,N-diethyl-[beta] phenylethylamine, 1,2-dimethylimidazole, 2-methylimidazole etc.

It is preferable that the ratio by weight of the polyisocyanate to polyol is from 170 to 70, preferably from 130 to 80, based on 100 parts by weight of the polyol.

It is preferable that the ratio by weight of the catalyst is from 0.1 to 4 parts by weight, particularly preferably from 1 to 2 parts by weight, based on 100 parts by weight of the polyol.

Preferred blowing agents are water, hydrocarbon, fluorochlorocarbon, fluorocarbon, etc. The amount of the blowing agent is from 0.1 to 1.8 parts by weight, preferably from 0.3 to 1.6 parts by weight, and in particular from 0.8 to 1.6 parts by weight, based on 100 parts by weight of the polyol.

EXAMPLES

Example 1

Comparison 5852 g of tetrahydrofuran are used as initial charge at room temperature in a three-necked flask with stirrer and high-performance condenser, and "degassed" by stirring and passing nitrogen through the system for 10 minutes. 70.0 mg of tris(dibenzylideneacetone)dipalladium and 95.0 mg of 4,5-bis(diphenylphosphino)-9,9-dimethylxanthene are then added, and the mixture is stirred for a further 15 minutes with nitrogen flushing. 198 g of phosphinic acid in 198 g of water are then added, with stirring. Nitrogen is passed through the reaction mixture for a further 10 minutes.

The reaction solution is then transferred, under a counter-current of nitrogen, into a 2 liter Büchi reactor blanketed by nitrogen, and residual material is removed from the three-necked flask by rinsing twice with a little tetrahydrofuran. Ethylene at 2.5 bar is applied to the reactor while the reaction mixture is stirred (stirrer rotation rate about 1400 rpm), and the reaction mixture is heated to 80° C. (jacket temperature). After 56 g of ethylene have been absorbed, the system is cooled to room temperature and any unreacted ethylene is discharged and burnt.

The reaction mixture is then freed from the solvent on a rotary evaporator under conditions of at most 60° C. and from 350 to 10 mbar. 300 g of deionized water (amount of theoretical yield times 1) is admixed with the residue and the mixture is stirred under nitrogen at room temperature for 1 hour. The resultant residue is filtered, and the filtrate is extracted with 200 ml of toluene. The aqueous phase is freed from the solvent on a rotary evaporator under conditions of at most 60° C. and from 250 to 10 mbar.

$^{31}$P NMR (D$_2$O, coupled): Multiplet doublet, 36.7 ppm

Example 2

198 g of phosphonic acid, 365 g of tetrahydrofuran, 198 g of water, 84 g of ethylene, 1.4 mg of tris(dibenzylideneacetone)dipalladium, and 1.9 mg of 4,5-bis(diphenyl-phosphino)-9,9-dimethylxanthene are reacted as in Example 1. Table 1 lists the precise conditions and yields.

Example 3

198 of phosphinic acid, 365 g of tetrahydrofuran, 198 g of water, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 4

198 g of phosphinic acid, 365 g of tetrahydrofuran, 198 g of water, 84 g of ethylene, 1 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 5

198 g of phosphinic acid, 365 g of tetrahydrofuran, 198 g of water, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 6

198 g of phosphinic acid, 365 g of tetrahydrofuran, 198 g of water, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 7

198 g of phosphinic acid, 365 g of tetrahydrofuran, 198 g of water, 84 g of ethylene, 1.4 mg of tris(dibenzylideneacetone)dipalladium, and 1.9 mg of 4,5-bis(diphenyl-phosphino)-9,9-dimethylxanthene are reacted as in Example 1. Table 1 lists the precise conditions and yields.

Example 8

198 g of phosphinic acid, 365 g of tetrahydrofuran, 198 g of water, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 9

1.98 g of phosphinic acid, 3.65 g of tetrahydrofuran, 1.98 g of water, 0.84 g of ethylene, 13.7 mg of tris(dibenzylideneacetone)dipalladium, and 19.1 g of 4,5-bis(diphenylphosphino)-9,9-dimethylxanthene are reacted as in Example 1. Table 1 lists the precise conditions and yields.

Example 10

198 g of phosphinic acid, 365 g of tetrahydrofuran, 198 g of water, 84 g of ethylene, 1.4 g of tris(dibenzylideneacetone)dipalladium, and 1.9 g of 4,5-bis(diphenylphosphino)-9,9-dimethylxanthene are reacted as in Example 1. Table 1 lists the precise conditions and yields.

Example 11

198 g of phosphinic acid, 365 g of tetrahydrofuran, 198 g of water, 84 g of ethylene, 0.014 mg of tris(dibenzylideneacetone)dipalladium, and 0.019 mg of 4,5-bis(diphenylphosphino)-9,9-dimethylxanthene are reacted as in Example 1. Table 1 lists the precise conditions and yields.

Example 12

198 g of phosphinic acid, 365 g of tetrahydrofuran, 198 g of water, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 13

198 g of phosphinic acid, 365 g of tetrahydrofuran, 198 g of water, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 14

198 g of phosphinic acid, 365 g of tetrahydrofuran, 198 g of water, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 15

198 g of phosphinic acid, 563 g of water, 84 g of ethylene, 0.6 mg of palladium(II) sulfate, and 6.8 mg of tris(3-sulfophenyl)phosphine trisodium salt are reacted as in Example 1. Table 1 lists the precise conditions and yields.

Example 16

198 g of phosphinic acid, 563 g of acetic acid, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 17

198 g of phosphinic acid, 365 g of toluene, 198 g of water, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 18

198 g of phosphinic acid, 563 g of butanol, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 19

198 g of phosphinic acid, 84 g of ethylene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 20

198 g of phosphinic acid, 365 g of tetrahydrofuran, 198 g of water, 252 g of hexene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 21

198 g of phosphinic acid, 365 g of tetrahydrofuran, 198 g of water, 312 g of styrene, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 22

198 g of phosphinic acid, 365 g of tetrahydrofuran, 198 g of water, 81 g of butadiene, 1.4 mg of tris(dibenzylideneacetone)dipalladium, and 1.9 mg of 4,5-bis(diphenylphosphino)-9,9-dimethylxanthene are reacted as in Example 3. Table 1 lists the precise conditions and yields.

Example 23

198 g of phosphinic acid, 365 of tetrahydrofuran, 198 g of water, 216 g of acrylic acid, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 24

198 g of phosphinic acid, 365 g of tetrahydrofuran, 198 g of water, 258 g of vinyl acetate, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 25

198 g of phosphinic acid, 365 g of tetrahydrofuran, 198 g of water, 171 g of allylamine, 1.4 mg of tris(dibenzylideneacetone)dipalladium, and 1.9 mg of 4,5-bis(diphenylphosphino)-9,9-dimethylxanthene are reacted as in Example 1. Table 1 lists the precise conditions and yields.

Example 26

198 g of phosphinic acid, 365 g of tetrahydrofuran, 198 g of water, 84 g of ethylene, 1.7 mg of bis(dibenzylideneacetone)palladium, and 1.2 mg of 1,3-bis(diphenylphosphino)propane are reacted as in Example 1. Table 1 lists the precise conditions and yields.

Example 27

198 g of phosphinic acid, 365 g of tetrahydrofuran, 198 g of water, 84 g of ethylene, 3.5 mg of tetrakis(triphenylphosphine)palladium, and 1.7 mg of 4,6-bis(diphenylphosphine)phenoxazine are reacted as in Example 1. Table 1 lists the precise conditions and yields.

Example 28

198 g of phosphinic acid, 365 g of tetrahydrofuran, 198 g of water, 84 g of ethylene, 3.2 mg of palladium on carbon, and 1.6 mg of triphenylphosphine are reacted as in Example 1. Table 1 lists the precise conditions and yields.

Example 29

198 g of phosphinic acid, 365 g of tetrahydrofuran, 198 g of water, 84 g of ethylene, 0.6 mg of palladium(II) sulfate, and 2.0 mg of triphenylphosphine bound on polystyrene are reacted as in Example 1. Table 1 lists the precise conditions and yields.

Example 30

198 g of phosphinic acid, 365 g of tetrahydrofuran, 198 g of water, 84 g of ethylene, 0.7 mg of palladium(II) acetate, and 2.1 mg of (oxy-2,1-phenylene)bis(diphenylphosphine) are reacted as in Example 1. Table 1 lists the precise conditions and yields.

Example 31

198 g of phosphinic acid, 365 g of tetrahydrofuran, 198 g of water, 84 g of ethylene, 3.7 mg of tetrakis(triphenylphosphine)platinum, and 2.1 mg of (R)(+)-2,2'-bis(diphenylphosphino)-1,1'-binaphthalene are reacted as in Example 1. Table 1 lists the precise conditions and yields.

Example 32

198 g of phosphinic acid, 365 of tetrahydrofuran, 198 g of water, 84 g of ethylene, 11.7 mg of platinum on alumina, and 2.4 mg of 1,2-bis(diphenylphosphino)ethane are reacted as in Example 1. Table 1 lists the precise conditions and yields.

Example 33

198 g of phosphinic acid, 365 g of tetrahydrofuran, 198 g of water, 84 g of ethylene, 0.4 mg of nickel dichloride, and 1.7 mg of 4,5-bis(diphenylphosphino)-9,9-dimethylxanthene are reacted as in Example 1. Table 1 lists the precise conditions and yields.

Example 34

198 g of phosphinic acid, 365 g of tetrahydrofuran, 198 g of water, 84 g of ethylene, 3.3 mg of tetrakis(triphenylphosphine)nickel, and 1.7 mg of 1,1'-bis(diphenylphosphino)ferrocene were reacted as in Example 1. Table 1 lists the precise conditions and yields.

Example 35

198 g of phosphinic acid sodium salt, 563 g of acetic acid, 84 g of ethylene, 0.9 mg of tris(dibenzylideneacetone)dipalladium, and 1.2 mg of 4,5-bis(diphenylphosphino)-9,9-dimethylxanthene are reacted as in Example 1. Table 1 lists the precise conditions and yields.

Example 36

198 g of butyl phosphinate, 365 g of tetrahydrofuran, 198 g of water, 84 g of ethylene, 0.7 mg of tris(dibenzylideneacetone)dipalladium, and 0.9 mg of 4,5-bis(diphenylphosphino)-9,9-dimethylxanthene are reacted as in Example 1. Table 1 lists the precise conditions and yields.

Example 37

198 g of ammonium hypophosphite, 365 g of tetrahydrofuran, 198 g of water, 84 g of ethylene, 1.1 mg of tris(dibenzylideneacetone)dipalladium, and 1.5 mg of 4,5-bis(diphenylphosphino)-9,9-dimethylxanthene are reacted as in Example 1. Table 1 lists the precise conditions and yields.

TABLE 1

| Example | P source | g | Solvent | g | Olefin | g | Transition metal | mg | Ligand | mg | T °C. |
|---|---|---|---|---|---|---|---|---|---|---|---|
| 1 (comp) | P1 | 198 | S1 | 6050 | O1 | 56.0 | T1 | 70.0 | L1 | 95.0 | 80 |
| 2 | P1 | 198 | S1 | 563 | O1 | 84.0 | T1 | 1.4 | L1 | 1.9 | 80 |
| 3 | P1 | 198 | S1 | 563 | O1 | 84.0 | T1 | 1.4 | L1 | 1.9 | 20 |
| 4 | P1 | 198 | S1 | 563 | O1 | 84.0 | T1 | 1.4 | L1 | 1.9 | 80 |
| 5 | P1 | 198 | S1 | 563 | O1 | 84.0 | T1 | 1.4 | L1 | 1.9 | 80 |
| 6 | P1 | 198 | S1 | 11 260 | O1 | 84.0 | T1 | 1.4 | L1 | 1.9 | 80 |
| 7 | P1 | 198 | S1 | 563 | O1 | 336.0 | T1 | 1.4 | L1 | 1.9 | 80 |
| 8 | P1 | 198 | S1 | 563 | O1 | 21.0 | T1 | 1.4 | L1 | 1.9 | 80 |
| 9 | P1 | 1.98 | S1 | 5.63 | O1 | 0.8 | T1 | 13 740.0 | L1 | 19 107.0 | 80 |
| 10 | P1 | 198 | S1 | 563 | O1 | 84.0 | T1 | 1374.0 | L1 | 1910.7 | 80 |
| 11 | P1 | 198 | S1 | 563 | O1 | 84.0 | T1 | 0.0014 | L1 | 0.0019 | 80 |
| 12 | P1 | 198 | S1 | 563 | O1 | 84.0 | T1 | 1.4 | L1 | 6.9 | 80 |
| 13 | P1 | 198 | S1 | 563 | O1 | 84.0 | T1 | 1.4 | L1 | 1.9 | 80 |
| 14 | P1 | 198 | S1 | 563 | O1 | 84.0 | T1 | 1.4 | L1 | 1.9 | 80 |
| 15 | P1 | 198 | S2 | 563 | O1 | 84.0 | T5 | 0.6 | L9 | 6.8 | 200 |
| 16 | P1 | 198 | S3 | 563 | O1 | 84.0 | T1 | 1.4 | L1 | 1.9 | 80 |
| 17 | P1 | 198 | S4 | 563 | O1 | 84.0 | T1 | 1.4 | L1 | 1.9 | 80 |
| 18 | P1 | 198 | S5 | 563 | O1 | 84.0 | T1 | 1.4 | L1 | 1.9 | 80 |
| 19 | P1 | 198 | — | 0 | O1 | 84.0 | T1 | 1.4 | L1 | 1.9 | 80 |
| 20 | P1 | 198 | S1 | 563 | O2 | 252.0 | T1 | 1.4 | L1 | 1.9 | 80 |
| 21 | P1 | 198 | S1 | 563 | O3 | 312.0 | T1 | 1.4 | L1 | 1.9 | 80 |
| 22 | P1 | 198 | S1 | 563 | O4 | 81.0 | T1 | 1.4 | L1 | 1.9 | 80 |
| 23 | P1 | 198 | S1 | 563 | O5 | 216.0 | T1 | 1.4 | L1 | 1.9 | 80 |
| 24 | P1 | 198 | S1 | 563 | O6 | 258.0 | T1 | 1.4 | L1 | 1.9 | 80 |
| 25 | P1 | 198 | S1 | 563 | O7 | 171.0 | T1 | 1.4 | L1 | 1.9 | 80 |
| 26 | P1 | 198 | S1 | 563 | O1 | 84.0 | T2 | 1.7 | L5 | 1.2 | 80 |
| 27 | P1 | 198 | S1 | 563 | O1 | 84.0 | T3 | 3.5 | L3 | 1.7 | 80 |
| 28 | P1 | 198 | S1 | 563 | O1 | 84.0 | T4 | 3.2 | L8 | 1.6 | 80 |
| 29 | P1 | 198 | S1 | 563 | O1 | 84.0 | T5 | 0.6 | L10 | 2.0 | 80 |
| 30 | P1 | 198 | S1 | 563 | O1 | 84.0 | T6 | 0.7 | L2 | 2.1 | 80 |
| 31 | P1 | 198 | S1 | 563 | O1 | 84.0 | T7 | 3.7 | L7 | 2.1 | 80 |
| 32 | P1 | 198 | S1 | 563 | O1 | 84.0 | T8 | 11.7 | L6 | 2.4 | 80 |
| 33 | P1 | 198 | S1 | 563 | O1 | 84.0 | T9 | 0.4 | L1 | 1.7 | 80 |
| 34 | P1 | 198 | S1 | 563 | O1 | 84.0 | T10 | 3.3 | L4 | 1.7 | 80 |
| 35 | P2 | 198 | S3 | 563 | O1 | 84.0 | T1 | 0.9 | L1 | 1.2 | 80 |
| 36 | P3 | 198 | S1 | 563 | O1 | 84.0 | T1 | 0.7 | L1 | 0.9 | 80 |
| 37 | P4 | 198 | S1 | 563 | O1 | 84.0 | T1 | 1.1 | L1 | 1.5 | 80 |

TABLE 1-continued

| Example | p bar | t h | Sequence S-P-O-T-L | S/P | O/P | T/P *10⁻⁶ | L/P *10⁻⁶ | Yield g | Yield % |
|---|---|---|---|---|---|---|---|---|---|
| 1 (comp) | 2.5 | 6 | 1-1-2-3-3 | 30.6 | 0.7 | 50.9 | 54.7 | 132.5 | 47.0 |
| 2 | 2.5 | 6 | 1-3-4-2-2 | 2.8 | 1.0 | 1.0 | 1.1 | 282.0 | 100.0 |
| 3 | 2.5 | 6 | 1-3-4-2-2 | 2.8 | 1.0 | 1.0 | 1.1 | 191.8 | 68.0 |
| 4 | 2.5 | 0.5 | 1-3-4-2-2 | 2.8 | 1.0 | 1.0 | 1.1 | 188.9 | 67.0 |
| 5 | 2.5 | 12 | 1-3-4-2-2 | 2.8 | 1.0 | 1.0 | 1.1 | 265.1 | 94.0 |
| 6 | 2.5 | 6 | 1-3-4-2-2 | 20.0 | 1.0 | 1.0 | 1.1 | 256.6 | 91.0 |
| 7 | 2.5 | 6 | 1-3-4-2-2 | 2.8 | 4.0 | 1.0 | 1.1 | 245.3 | 87.0 |
| 8 | 2.5 | 6 | 1-3-4-2-2 | 2.8 | 0.25 | 1.0 | 1.1 | 67.7 | 24.0 |
| 9 | 2.5 | 6 | 1-3-4-2-2 | 2.8 | 1.0 | 1 000 000.0 | 1 100 000.0 | 2.5 | 89.0 |
| 10 | 2.5 | 6 | 1-3-4-2-2 | 2.8 | 1.0 | 1000.0 | 1100.0 | 262.3 | 93.0 |
| 11 | 2.5 | 6 | 1-3-4-2-2 | 2.8 | 1.0 | 0.01 | 0.01 | 214.3 | 76.0 |
| 12 | 2.5 | 6 | 1-3-4-2-2 | 2.8 | 1.0 | 1.0 | 4.0 | 256.6 | 91.0 |
| 13 | 2.5 | 6 | 1-2-5-4-3 | 2.8 | 1.0 | 1.0 | 1.1 | 273.5 | 97.0 |
| 14 | 2.5 | 6 | 2-5-4-3-1 | 2.8 | 1.0 | 1.0 | 1.1 | 270.7 | 96.0 |
| 15 | 16.0 | 6 | 1-3-4-2-2 | 2.8 | 1.0 | 1.0 | 4.0 | 236.9 | 84.0 |
| 16 | 2.5 | 6 | 1-3-4-2-2 | 2.8 | 1.0 | 1.0 | 1.1 | 270.7 | 96.0 |
| 17 | 2.5 | 6 | 1-3-4-2-2 | 2.8 | 1.0 | 1.0 | 1.1 | 273.5 | 97.0 |
| 18 | 2.5 | 6 | 1-3-4-2-2 | 2.8 | 1.0 | 1.0 | 1.1 | 279.2 | 99.0 |
| 19 | 2.5 | 6 | 1-3-4-2-2 | 0.0 | 1.0 | 1.0 | 1.1 | 262.3 | 93.0 |
| 20 | 1.0 | 6 | 1-3-4-2-2 | 2.8 | 1.0 | 1.0 | 1.1 | 418.5 | 93.0 |
| 21 | 1.0 | 6 | 1-3-4-2-2 | 2.8 | 1.0 | 1.0 | 1.1 | 510.0 | 100.0 |
| 22 | 2.5 | 6 | 1-3-4-2-2 | 2.8 | 0.5 | 1.0 | 1.1 | 273.4 | 98.0 |
| 23 | 1.0 | 6 | 1-3-4-2-2 | 2.8 | 1.0 | 1.0 | 1.1 | 327.1 | 79.0 |
| 24 | 1.0 | 6 | 1-3-4-2-2 | 2.8 | 1.0 | 1.0 | 1.1 | 387.6 | 85.0 |
| 25 | 1.0 | 6 | 1-3-4-2-2 | 2.8 | 1.0 | 1.0 | 1.1 | 321.0 | 87.0 |
| 26 | 2.5 | 6 | 1-3-4-2-2 | 2.8 | 1.0 | 1.0 | 1.0 | 282.0 | 100.0 |
| 27 | 2.5 | 6 | 1-3-4-2-2 | 2.8 | 1.0 | 1.0 | 1.0 | 276.4 | 98.0 |
| 28 | 2.5 | 6 | 1-3-4-2-2 | 2.8 | 1.0 | 1.0 | 2.0 | 251.0 | 89.0 |
| 29 | 2.5 | 6 | 1-3-4-2-2 | 2.8 | 1.0 | 1.0 | 2.0 | 259.4 | 92.0 |
| 30 | 2.5 | 6 | 1-3-4-2-2 | 2.8 | 1.0 | 1.0 | 1.3 | 267.9 | 95.0 |
| 31 | 2.5 | 6 | 1-3-4-2-2 | 2.8 | 1.0 | 1.0 | 1.1 | 172.0 | 61.0 |
| 32 | 2.5 | 6 | 1-3-4-2-2 | 2.8 | 1.0 | 1.0 | 2.0 | 152.3 | 54.0 |
| 33 | 2.5 | 6 | 1-3-4-2-2 | 2.8 | 1.0 | 1.0 | 1.0 | 245.3 | 87.0 |
| 34 | 2.5 | 6 | 1-3-4-2-2 | 2.8 | 1.0 | 1.0 | 1.0 | 265.1 | 94.0 |
| 35 | 2.5 | 6 | 1-3-4-2-2 | 2.8 | 1.0 | 1.0 | 1.1 | 245.3 | 98.0 |
| 36 | 2.5 | 6 | 1-3-4-2-2 | 2.8 | 1.0 | 1.0 | 1.1 | 189.0 | 99.0 |
| 37 | 2.5 | 6 | 1-3-4-2-2 | 2.8 | 1.0 | 1.0 | 1.1 | 310.1 | 97.0 |

TABLE 2

| | P source P | | Solvent S | | Olefin O | | Transition metal T | | Ligand L |
|---|---|---|---|---|---|---|---|---|---|
| P1 | Phosphinic acid | S1 | Water/tetrahydrofuran | O1 | Ethylene | T1 | Tris(dibenzylideneacetone)-dipalladium | L1 | 4,5-Bis(diphenylphosphino)-9,9-dimethylxanthene |
| P2 | Phosphinic acid sodium salt | S2 | Water | O2 | Hexene | T2 | Bis(dibenzylideneacetone) palladium | L2 | (Oxy-2,1-phenylene)-bis(diphenylphosphine) |
| P3 | Butyl phosphinate | S3 | Acetic acid | O3 | Styrene | T3 | Tetrakis(triphenylphosphine)palladium | L3 | 4,6-Bis(diphenylphosphine)phenoxazine |
| P4 | Phosphinic acid ammonium salt | S4 | Water/toluene | O4 | Butadiene | T4 | Palladium on carbon | L4 | 1,1'-Bis(diphenylphosphino)-ferrocene |
| | | S5 | Butanol | O5 | Acrylic acid | T5 | Palladium(II) sulfate | L5 | 1,3-Bis(diphenylphosphino)propane |
| | | | | O6 | Vinyl acetate | T6 | Palladium(II) acetate | L6 | 1,2-Bis(diphenylphosphino)ethane |
| | | | | O7 | Allylamine | T7 | Tetrakis(triphenyl-phosphine)platinum | L7 | (R)(+)-2,2'-Bis(diphenylphosphino)-1,1'-binaphthalene |
| | | | | | | T8 | Platinum on alumina | L8 | Triphenylphosphine |
| | | | | | | T9 | Nickel dichloride | L9 | Tris(3-sulfophenyl)phosphine trisodium salt |
| | | | | | | T10 | Tetrakis(triphenyl-phosphine)nickel | L10 | Triphenylphosphine bound on polystyrene |

TABLE 3

| Example | Product |
|---|---|
| 1-19; 26-34 | Ethylphosphonous acid |
| 20 | 1-Hexylphosphonous acid |
| 21 | 2-Phenylethylphosphonous acid |
| 22 | 1,4-Butanediphosphonous acid |
| 23 | 3-Carboxyethylphosphonous acid |
| 24 | 2-Acetoethylphosphonous acid |
| 25 | 3-Aminopropylphosphonous acid |
| 35 | Ethylphosphonous acid sodium salt |

TABLE 3-continued

| Example | Product |
| --- | --- |
| 36 | Butyl ethylphosphonite |
| 37 | Ethylphosphonous acid ammonium salt |

The invention claimed is:

1. A process for the production of an alkylphosphonous acid, alkylphosphonous salt or alkylphosphonous ester, comprising the step of reacting a source of phosphinic acid with one or more olefins in the presence of a catalyst or a catalyst system, and where the source of phosphinic acid is phosphinic acid, a salt of phosphinic acid, an ester of phosphinic acid, or a mixture of these, wherein the catalyst is a transition metal, transition metal compound or wherein the catalyst system is a transition metal, a transition metal compound, and at least one ligand, wherein the one or more olefins are ethylene, 1-propylene, 1-butene, 1,3-butadiene, 3 methyl-but-1-ene or a mixture thereof, wherein the transition metal and transition metal compound are rhodium, nickel, palladium, platinum or a combination thereof and wherein the partial pressure of the olefin during the reaction is from 0.1 to 10 bar.

2. The process for the production of an alkylphosphonous acid, alkylphosphonous salt or alkylphosphonous ester, as claimed in claim 1, further comprising
   a) reacting the source of phosphinic acid with the olefin in the presence of a catalyst and optionally a solvent,
   b) optionally removing the solvent, the olefin or both,
   c) removing the catalyst, catalyst system, transition metal, transition metal compound,
   d) removing the ligand, complexing agent or both, and
   e) removing the auxiliary, olefin or both.

3. The process for the production of alkylphosphonous acid, alkylphosphonous salt or alkylphosphonous ester, as claimed in claim 1, further comprising
   a) reacting the source of phosphinic acid with olefins in the presence of a catalyst, and
   b) removing insoluble product by filtration.

4. The process for the production of an alkylphosphonous acid, alkylphosphonous salt or alkylphosphonous ester, as claimed in claim 1, further comprising
   a) reacting the source of phosphinic acid with olefins in the presence of a catalyst,
   b) optionally removing the catalyst,
   c) removing the ligand, complexing agent or both, and
   d) removing the solvent.

5. The process for the production of an alkylphosphonous acid, alkylphosphonous salt or alkylphosphonous ester, as claimed in claim 1, further comprising
   a) reacting the source of phosphinic acid with olefins in the presence of a catalyst,
   b) optionally removing the catalyst,
   c) removing the ligand, complexing agent or both, and
   d) removing the solvent,
   e) at least 90% of the complexing agent, the ligand, catalyst or any combination thereof that has been removed is returned to step a).

6. The process as claimed in claim 1, wherein the salt of phosphinic acid is an alkali metal salt, an alkaline earth metal salt, a salt of the elements of the third or fourth main group and of the second, fourth, or eighth transition group, or of the lanthanoid group, an ammonium salt, or a primary, secondary, tertiary, or quaternary alkyl- or arylammonium salt.

7. The process as claimed in claim 1, wherein the catalyst system is formed via reaction of a transition metal a transition metal compound, and at least one ligand.

8. The process for the production of an alkylphosphonous acid, alkylphosphonous salt or alkylphosphonous ester as claimed in claim 1, wherein the phosphinic acid is hypophosphorous acid $H_3PO_2$.

* * * * *